US010449389B2

(12) United States Patent
Ollila et al.

(10) Patent No.: US 10,449,389 B2
(45) Date of Patent: Oct. 22, 2019

(54) DYNAMIC TARGET MASKER IN RADIATION TREATMENT OF MULTIPLE TARGETS

(71) Applicant: Varian Medical Systems International AG, Cham (CH)

(72) Inventors: Santtu Ollila, Helsinki (FI); Mikko Vainio, Espoo (FI); Jarkko Peltola, Tuusula (FI); Janne Nord, Espoo (FI)

(73) Assignee: Varian Medical Systems International AG, Cham (CH)

( * ) Notice: Subject to any disclaimer, the term of this patent is extended or adjusted under 35 U.S.C. 154(b) by 125 days.

(21) Appl. No.: 15/831,210

(22) Filed: Dec. 4, 2017

(65) Prior Publication Data

US 2018/0154179 A1    Jun. 7, 2018

Related U.S. Application Data

(60) Provisional application No. 62/430,272, filed on Dec. 5, 2016.

(51) Int. Cl.
  *A61N 5/10*          (2006.01)
(52) U.S. Cl.
  CPC ......... *A61N 5/1036* (2013.01); *A61N 5/1031* (2013.01); *A61N 5/1045* (2013.01);
  (Continued)
(58) Field of Classification Search
  CPC .. A61N 5/1036; A61N 5/1045; A61N 5/1047; A61N 5/1065; A61N 5/1031; G06F 19/325

See application file for complete search history.

(56) References Cited

U.S. PATENT DOCUMENTS 9,443,633 B2 *   9/2016   Orton ..................... G21K 1/046
RE46,953 E *     7/2018   Yu ........................... A61N 5/103
(Continued)

FOREIGN PATENT DOCUMENTS

WO    2013075743    5/2013
WO    2015039903    3/2015

OTHER PUBLICATIONS

International Application No. PCT/EP2017/081492, "International Search Report and Written Opinion", dated Feb. 16, 2018, 11 pages.

*Primary Examiner* — Kiho Kim
(74) *Attorney, Agent, or Firm* — Kilpatrick Townsend & Stockton LLP

(57) ABSTRACT

A method for determining MLC leaf sequences for radiation treatment includes obtaining BEV projections of a first target volume and a second target volume along one or more treatment paths of a radiation treatment plan, analyzing the BEV projections to determine one or more contiguous ranges of spatial points where there exists an interstitial region between the first target volume and the second target volume in the direction of MLC leaf motion, and determining a first set of MLC leaf sequences such that an aperture formed by the MLC in a first portion of the one or more contiguous ranges of spatial points exposes radiation to the first target volume but not the second target volume, and an aperture formed by the MLC in a second portion of the one or more contiguous ranges of spatial points exposes radiation to the second target volume but not the first target volume.

20 Claims, 20 Drawing Sheets

(52) U.S. Cl.
CPC ......... *A61N 5/1047* (2013.01); *A61N 5/1065* (2013.01); *A61N 2005/1032* (2013.01)

(56) References Cited

U.S. PATENT DOCUMENTS

| | | | |
|---|---|---|---|
| 2010/0177870 A1 | 7/2010 | Nord et al. | |
| 2012/0230462 A1* | 9/2012 | Robar | A61N 5/1049 378/4 |
| 2013/0197878 A1* | 8/2013 | Fiege | A61N 5/1031 703/2 |
| 2015/0265851 A1* | 9/2015 | Ma | A61N 5/1031 600/1 |
| 2015/0335914 A1* | 11/2015 | Otto | A61N 5/103 600/1 |
| 2018/0221685 A1* | 8/2018 | Eriksson | G16H 50/20 |

* cited by examiner

DYNAMIC TARGET MASKER IN RADIATION TREATMENT OF MULTIPLE TARGETS

CROSS-REFERENCE TO RELATED APPLICATIONS

The present application is a non-provisional application of and claims the benefit and priority under 35 U.S.C. 119(e) of U.S. Provisional Application No. 62/430,272, filed Dec. 5, 2016 entitled "PRODUCING CONFORMAL MLC SEQUENCES ABOUT TARGETS IN CONCURRENT RADIATION TREATMENT OF MULTIPLE TARGETS," the entire content of which is incorporated herein by reference for all purposes.

BACKGROUND

Modern radiation therapy techniques include the use of Intensity Modulated Radiotherapy ("IMRT"), typically by means of an external radiation treatment system, such as a linear accelerator, equipped with a multi-leaf collimator ("MLC"). Use of multi-leaf collimators in general, and an IMRT field in particular, allows the radiologist to treat a patient from a given direction of incidence to the target while varying the shape and dose of the radiation beam, thereby providing greatly enhanced ability to deliver radiation to a target within a treatment volume while avoiding excess irradiation of nearby healthy tissue. However, the greater freedom IMRT and other complex radiotherapy techniques, such as volumetric modulated arc therapy (VMAT, where the system gantry moves while radiation is delivered) and three-dimensional conformal radiotherapy ("3D conformal" or "3DCRT"), afford to radiologists has made the task of developing treatment plans more difficult. As used herein, the term radiotherapy should be broadly construed and is intended to include various techniques used to irradiate a patient, including use of photons (such as high energy x-rays and gamma rays), particles (such as electron and proton beams), and radiosurgical techniques. While modern linear accelerators use MLCs, other methods of providing conformal radiation to a target volume are known and are within the scope of the present invention.

Several techniques have been developed to create radiation treatment plans for IMRT or conformal radiation therapy. Generally, these techniques are directed to solving the "inverse" problem of determining the optimal combination of angles, radiation doses and MLC leaf movements to deliver the desired total radiation dose to the target, or possibly multiple targets, while minimizing irradiation of healthy tissue. This inverse problem is even more complex for developing arc therapy plans where the gantry is in motion while irradiating the target volume. Heretofore, radiation oncologists or other medical professionals, such as medical physicists and dosimetrists, have used one of the available algorithms to develop and optimize a radiation treatment plan.

When treating multiple targets concurrently using volumetric modulated arc therapy (VMAT), a conflict may arise when there are two or more targets separated from each other under a single pair of MLC leaves for a certain portion of a VMAT arc. If the aperture formed by the MLC leaf pair is wide enough so as to expose all participating targets, normal tissue located in a region between the participating targets may receive unwanted radiation doses. Therefore, it is desirable to generate MLC sequences that can minimize radiation exposure to normal tissue located in the region between the participating targets.

SUMMARY

Embodiments of the present invention relate generally to determining MLC leaf sequences in a concurrent treatment of multiple targets, and more particularly to a method of determining conformal MLC leaf sequences using a dynamic target masker approach to resolve conflicts among the multiple targets.

According to some embodiments, a method for determining multi-leaf collimator (MLC) leaf sequences in a radiation treatment plan for concurrent treatment of multiple target volumes may include receiving information about a first target volume and a second target volume, and receiving a radiation treatment plan including one or more treatment paths. Each treatment path may define a respective trajectory of spatial points. The one or more treatment paths may correspond to an MLC angle defining a direction of leaf motion of a MLC. The method may further include obtaining beam's-eye view (BEV) projections of the first target volume and the second target volume along the one or more treatment paths based on the information about a first target volume and a second target volume, and analyzing the BEV projections of the first target volume and the second target volume to determine one or more contiguous ranges of spatial points along the one or more treatment paths where there exists an interstitial region between a boundary of the first target volume and a boundary of the second target volume in the direction of MLC leaf motion. The method may further include determining a first set of MLC leaf sequences for the one or more treatment paths such that an aperture formed by the MLC in a first portion of the one or more contiguous ranges of spatial points exposes radiation to the first target volume but not the second target volume, and an aperture formed by the MLC in a second portion of the one or more contiguous ranges of spatial points exposes radiation to the second target volume but not the first target volume.

Other embodiments are directed to systems and computer readable media associated with methods described herein.

A better understanding of the nature and advantages of embodiments of the present invention may be gained with reference to the following detailed description and the accompanying drawings.

TERMS

Figure 1:
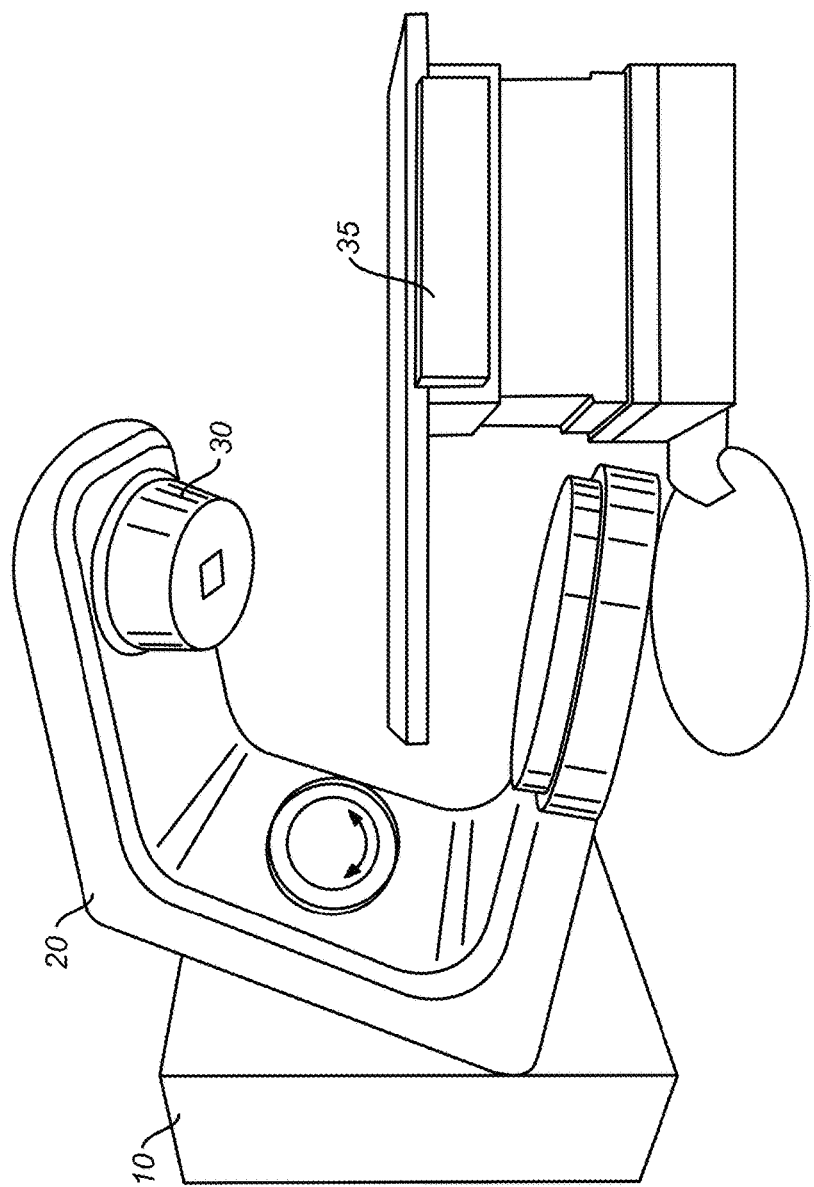
FIG. 1 is a schematic perspective view of a radiation treatment system.

"Radiation" refers to any particles (e.g., photons, electrons, protons etc.) used to treat tissue, e.g., tumors. Examples of radiation include high energy x-rays, gamma rays, electron beams, and proton beams. The different particles can correspond to different types of radiation treatments. The "treatment volume" refers to the volume that will be subjected to radiation, and is sometimes referred to as the "irradiated volume." The "target structure", "target volume", and "planning target volume" ("PTV") refer to tissue intended to receive a therapeutic prescribed dose.

A "radiation treatment plan" can include a dose distribution, machine parameters for achieving the dose distribution for a given patient, and information about the given patient. A dose distribution provides information about the variation in the radiation dose with spatial positions within a treatment area of the patient. A "dose distribution" can take many forms, e.g., a dose volume histogram (DVH) or a dose matrix. A DVH can summarize three-dimensional (3D) dose distributions in a graphical 2D format, e.g., where the horizontal axis is the dose (e.g., in units of grays—Gy) absorbed by the target structure (e.g., a tumor) and the vertical axis is the volume percentage. In a differential DVH, the height of a bar at a particular dose indicates the volume of the target structure receiving the particular dose. In a cumulative DVH, the height of a bar at a particular dose represents the volume of the structure receiving greater than or equal to that dose. The cumulative DVH is generally a curve (e.g., when small bin sizes are used), whereas the differential DVH is generally a disjoint bar graph. A drawback of a DVH is that it offers no spatial information; i.e., a DVH does not show where within a structure a dose is received. A dose matrix can provide the dose that each part of the body receives.

The term "spatial point" used in this disclosure in relation to a treatment field refers to a geometrical point associated with a set of values for treatment axes coordinates of an external-beam radiation treatment system. A spatial point is defined by the position of the isocenter, the position and angles of the patient support, and the gantry angle. The term "control point" refers to a parametrical point of a radiation treatment field that includes spatial information about the treatment axes as well as the MU count and/or the related concept of the meter set weight.

In this disclosure, a "treatment path" may refer to a treatment field trajectory where the direction of incidence to the treatment target changes while radiation is administered. For example, a treatment path can include a VMAT arc in which radiation is administered with simultaneous gantry rotation and MLC motion. A treatment path can also include a VMAT arc where the isocenter changes along the path of the arc. A VMAT arc can be either coplanar or non-coplanar. A coplanar VMAT arc refers to the case where the couch rotation angle is fixed at zero degree as the gantry rotates during beam-on. A non-coplanar VMAT arc refers to the case where the couch rotation angle is fixed at a non-zero degree angle as the gantry rotates during beam-on, i.e., the couch is not parallel to the axis of rotation of the gantry. A VMAT arc can also include a coronal arc where the gantry is fixed and the couch rotates during continuous irradiation.

A field trajectory of a treatment path may be defined by the movements of the treatment axes of the external-beam radiation treatment system, such as the position of the isocenter, the position and angles of the patient support, and the gantry angle. According to embodiments of the present invention, it is assumed that the field trajectories of the treatment paths, as well as the collimator angle, are predetermined and are treated as input. The method of dynamic target masking is applied to determine the MLC leaf sequences for the predetermined treatment paths.

"Beam's eye view" (BEV) is an imaging technique that can be used in radiation therapy for quality assurance and planning of external beam radiation therapy treatments. A BEV image can contain the images of a patient's anatomy and beam modifiers (such as jaws or multi-leaf collimators).

DETAILED DESCRIPTION

The present disclosure relates generally to treatment planning for radiation therapy using external-beam radiation treatment systems, and is more particularly directed to methods for producing conformal multi-leaf collimator (MLC) sequences in concurrent treatment of multiple treatment targets using a dynamic target masker technique.

Clinical goals of a radiation treatment may include delivering prescribed radiation dose to a treatment target while keeping the amount of radiation dose to the healthy tissues surrounding the target to a minimum. Therefore, it is usually desirable to generate MLC sequence such that an aperture formed by the MLC conforms to the contour of the target, so that the normal tissue surrounding the target is exposed to as little radiation as possible. This is especially important in treatment of brain tumors as the target is contained within normal brain tissue, which is itself an organ at risk. When treating multiple targets concurrently using volumetric modulated arc therapy (VMAT), a conflict may arise when there are more than one targets under a single pair of leaves in the multi-leaf collimator (MLC).

Embodiments may perform target masking dynamically within a VMAT optimizer. A VMAT optimizer is an advantageous phase in the treatment plan optimization for deciding where in the control point sequence and which targets to mask out and which to irradiate, as the optimizer has the most information (e.g., fluence, dose, dose rates, optimization objectives, and MLC and other mechanical constraints of the treatment device) for making the decision.

Embodiments may be able to resolve conflicts dynamically during the VMAT optimization, and can make use of the fluence, which may be based on user-specified optimization objectives. In some embodiments, a self-improving feedback loop may be included as follows: (a) a decision to mask out some targets at some control points is made; (b) the fluence and the MLC sequences in the mask-modified section is reoptimized, which may provide a subsequence candidate; (c) the total cost function of the optimizer may be evaluated, if there is an improvement, the change may be kept and the actual MLC sequence may be modified according to the subsequence candidate; and (d) if at a later stage of the optimization, the metrics based on fluence, dose and the optimization objectives indicate that further improvement of the treatment plan is possible by canceling a previous masking, and it is possible in terms of the machine constraints, it can be done.

In general, radiation therapy includes the use of ionizing radiation to treat living tissue, usually tumors. There are many different types of ionizing radiation used in radiation therapy, including high energy x-rays, electron beams, and proton beams. The process of administering the radiation to a patient can be somewhat generalized regardless of the type of radiation used.

External beam therapy (EBT), also called external radiation therapy, is a method for delivering a beam or several beams of high-energy x-rays to a patient's tumor. Beams are generated outside the patient (usually by a linear accelerator) and are targeted at the tumor site.

I. Treatment System

Figure 2:
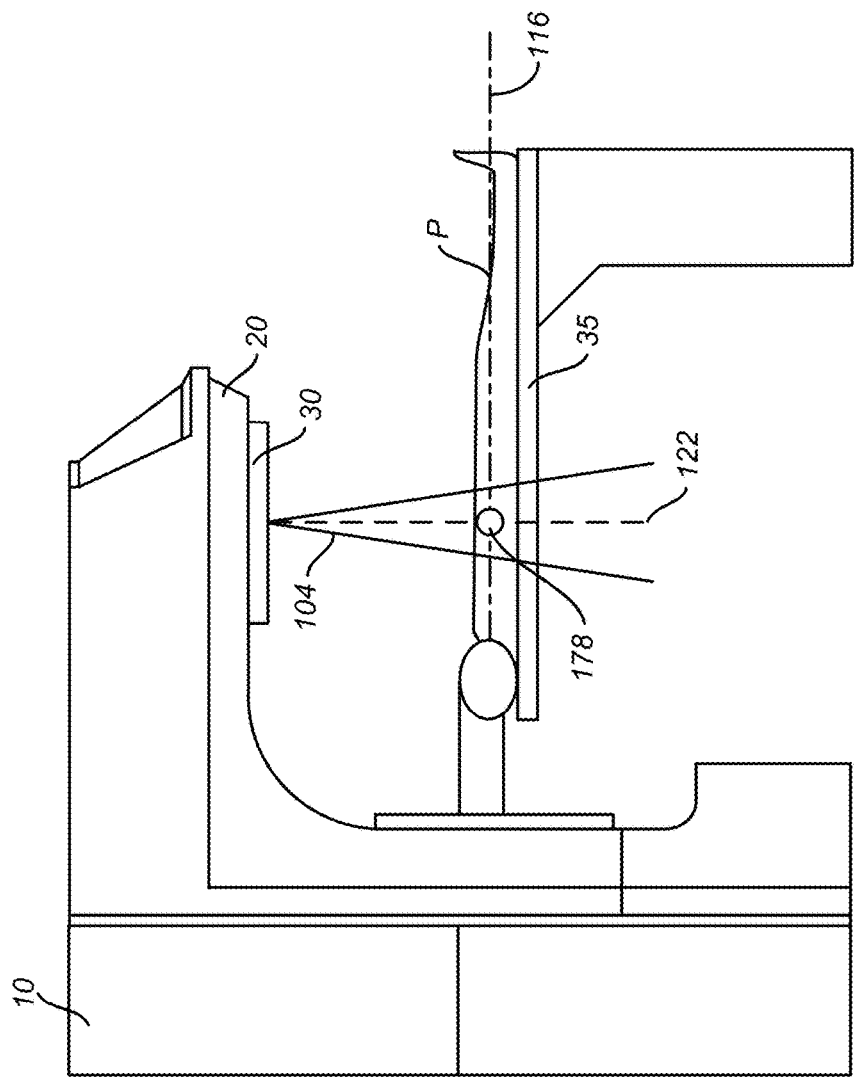
FIG. 2 is a schematic side view of a radiation treatment system.

FIGS. 1 and 2 depict a radiation treatment system of the type that may be used in connection with the present invention. Referring to FIG. 1, a perspective view of radiation treatment system (in this case a linear accelerator) is shown. Typically, such a system is capable of generating either an electron (particle) beam or an x-ray (photon) beam for use in the radiotherapy treatment of patients on a treatment couch 35. Other radiation treatment systems are capable of generating heavy ion particles such as protons. For purposes of the present discussion, only x-ray irradiation will be discussed. However, it will be appreciated by those skilled in the art that the same principles apply to other systems.

Stand 10 supports a rotatable gantry 20 with a treatment head 30. Next to stand 10 there is arranged a control unit (not shown) that includes control circuitry for controlling the different modes of operation of the accelerator. A high voltage source is provided within the stand or in the gantry, to supply voltage to an electron gun (not shown) positioned on an accelerator guide located in the gantry 20. Electrons are emitted from the electron gun into the guide (not shown) where they are accelerated. A source supplies RF (microwave) power for the generation of an electric field within the waveguide. The electrons emitted from the electron gun are accelerated in the waveguide by the electric field, and exit the waveguide as a high energy electron beam, typically at megavoltage energies. The electron beam then strikes a suitable metal target, emitting high energy x-rays in the forward direction.

Referring now to FIG. 2, a somewhat more detailed side view of a radiation treatment system of the type that may be used in connection with the present invention is shown. A patient P is shown lying on the treatment couch 35. X-rays formed as described above are emitted from the target in the treatment head 30 in a divergent beam 104. Typically, a patient plane 116, which is perpendicular to the page in FIG. 2, is positioned about one meter from the x-ray source or target, and the axis of the gantry 20 is located on the plane 116, such that the distance between the target and the isocenter 178 remains constant when the gantry 20 is rotated. The isocenter 178 is at the intersection between the patient plane 116 and the central axis of beam 122. A treatment volume to be irradiated is located about the isocenter 178.

Figure 3:
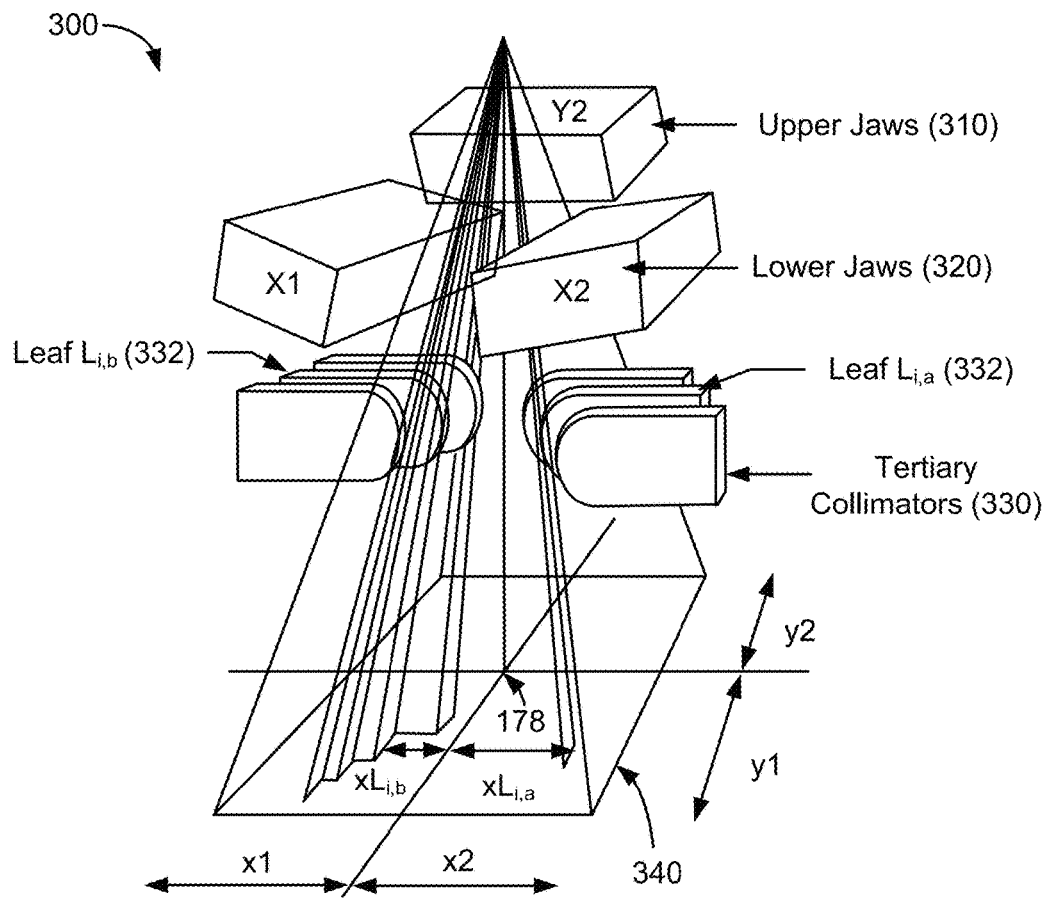
FIG. 3 shows schematically a photon collimation system in a radiation treatment system.

FIG. 3 shows schematically a photon collimation system 300 with upper jaws 310 (i.e., the Y1 and Y2 jaws; the Y1 jaw is omitted for clarity), lower jaws 320 (i.e., the X1 and X2 jaws), and a multi-leaf collimator (MLC) 330. The field dimensions in the plane 340 at the isocenter 178 are indicated. The upper jaws 310, the lower jaws 320, and the leaves 332 of the MLC 330 comprise an x-ray blocking material, and are positioned in the head 30 to define the width of the x-ray beam at the patient plane. Typically, the jaws 310 and 320 are movable and, when fully open, define a maximum beam of about 40 cm×40 cm at the patient plane 116. The MLC 330 is positioned at the exit of the head 30, to further shape the x-ray beam. Since its introduction in 1990 the MLC has become a standard feature of most radiation treatment systems. An example of a current MLC sold by the assignee of the present invention use up to 120 individually controllable leaves, typically thin slices of tungsten, that can be moved into or out of the x-ray beam under the control of system software.

Figure 4:
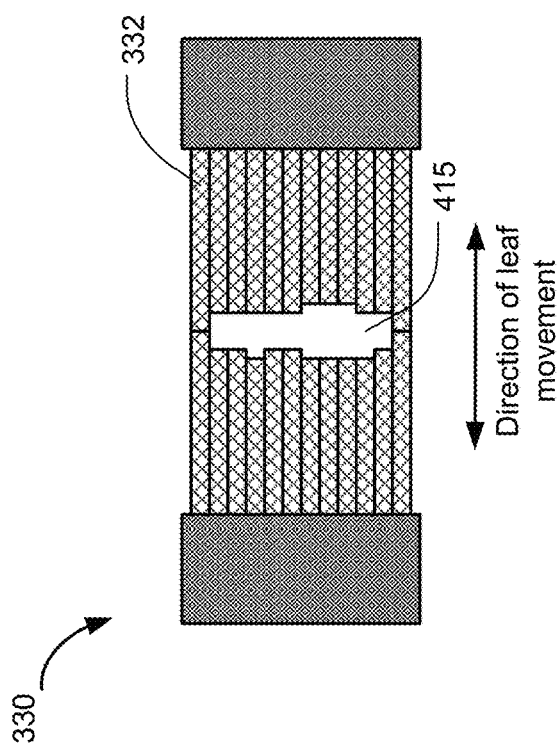
FIG. 4 shows an exemplary multi-leaf collimator (MLC) plane.

FIG. 4 shows an exemplary MLC plane having a plurality of leaves 332, arranged in opposing pairs, and an aperture 415 created by selected leaf movements. Radiation passes through and is shaped by the aperture 415. Thus, the MLC can be used to collimate the x-rays to provide conformal treatment of tumors from various angles ("3D conformal") as well as intensity modulated radiotherapy ("IMRT"), whereby different radiation doses are delivered to different portions of the treatment area. The treatment volume, i.e., the irradiated volume proximate to the isocenter 178 in the path of the x-ray beam, is defined by the jaws 310 and 320, the leaf sequences of the MLC 330, and the collimator angle, i.e., the angle at which the MLC 330 sits in the head 30. Some external radiation treatment systems may include multiple layers of MLCs. The multiple layers of MLCs may be positioned at different planes and at different collimator angles.

Figure 5:
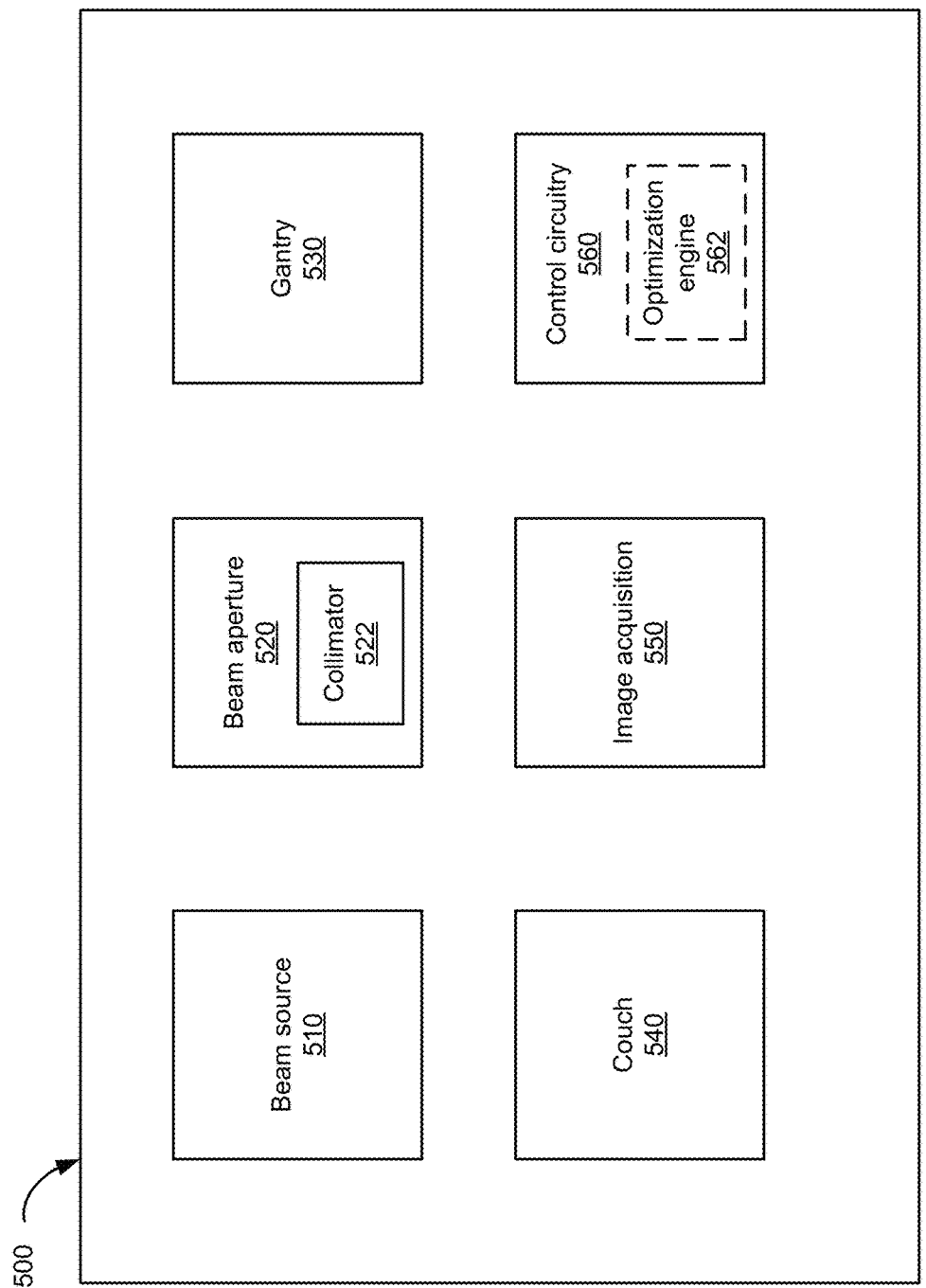
FIG. 5 shows a block diagram of an external-beam radiation treatment system of FIGS. 1 and 2.

FIG. 5 shows a block diagram of an external-beam radiation treatment system 500 of FIGS. 1 and 2. The radiation treatment system 500 includes a beam source 510, a beam aperture 520, a gantry 530, and a couch 540. The beam source 510 is configured to generate a beam of therapeutic radiation. This beam of radiation may include x-rays, particles, and the like. The beam aperture 520 includes an adjustable multi-leave collimator (MLC) 522 for spatially filtering the radiation beam. The couch 540 is configured to support and position a patient. The couch 540 may have six degrees of freedom, namely the translational offsets X, Y, and Z, and the rotation, pitch, and yaw.

The gantry 530 that circles about the couch 540 houses the beam source 510 and the beam aperture 520. The beam source 510 is optionally configured to generate imaging radiation as well as therapeutic radiation. The radiation treatment system 500 may further include an image acquisition system 550 that comprises one or more imaging detectors mounted to the gantry 530.

The radiation treatment system 500 further includes a control circuitry 560 for controlling the operation of the beam source 510, the beam aperture 520, the gantry 530, the couch 540, and the image acquisition system 550. The control circuitry 560 may include hardware, software, and memory for controlling the operation of these various components of the radiation treatment system 500. The control circuitry 560 can comprise a fixed-purpose hard-wired platform or can comprise a partially or wholly-programmable platform. The control circuitry 560 is configured to carry out one or more steps, actions, and other functions described herein. In some embodiments, the control circuitry 560 may include a memory for receiving and storing a radiation treatment plan that defines the control points of one or more treatment fields. The control circuitry 560 may then send control signals to the various components of the radiation treatment system 500, such as the beam source 510, the beam aperture 520, the gantry 530, and the couch 540, to execute the radiation treatment plan. In some embodiments, the control circuitry 560 may include an optimization engine 562 configured for determining a radiation treatment plan. In some other embodiments, the control circuitry 560 may not include an optimization engine. In those cases, a radiation treatment plan may be determined by an optimization engine in a separate computer system, and the radiation treatment plan is then transmitted to the control circuitry 560 of the radiation treatment system 500 for execution.

II. Radiation Treatment Planning

Radiation therapy is generally implemented in accordance with a radiation treatment plan that typically takes into account the desired dose of radiation that is prescribed to be delivered to the tumor, as well as the maximum dose of radiation that can be delivered to surrounding tissue. Various techniques for developing radiation treatment plans may be used. Preferably, the computer system used to develop the radiation treatment plan provides an output that can be used to control the radiation treatment system, including the control points and the MLC leaf movements. Typically, the desired dose prescribed in a radiation treatment plan is delivered over several sessions, called fractions.

Several techniques have been developed to create radiation treatment plans for IMRT or conformal radiation therapy. Generally, these techniques are directed to solving the "inverse" problem of determining the optimal combination of angles, radiation doses and MLC leaf movements to deliver the desired total radiation dose to the target while minimizing irradiation of healthy tissue. This inverse problem is even more complex for developing arc therapy plans, such as volumetric modulated arc therapy (VMAT), where the one or more external treatment coordinates, such as the isocenter location, gantry angle, couch angles, and couch offsets, are in motion while irradiating the target volume. Heretofore, radiation oncologists or other medical professionals, such as medical physicists and dosimetrists, have used one of the available algorithms to develop and optimize a radiation treatment plan.

Typically, such planning starts with volumetric information about the target tumor and about any nearby tissue structures. For example, such information may comprise a map of the planning target volume ("PTV"), such as a prostate tumor, which is prescribed by the physician to receive a certain therapeutic radiation dose with allowable tolerances. Volumetric information about nearby tissues may include for example, maps of the patient's bladder, spinal cord and rectum, each of which may be deemed an organ at risk (OAR) that can only receive a much lower, maximum prescribed amount of radiation. This volumetric information along with the prescribed dose limits and similar objectives set by the medical professionals are the basis for calculating an optimized dose distribution, also referred to as fluence map, which in turn is the basis for determining a radiation treatment plan. The volumetric information may, for example, be reduced to an objective function or a single figure of merit that accounts for the relative importance of various tradeoffs inherent in a radiation treatment plan, along with constraints that must be met for the radiation treatment plan to be medically acceptable or physically possible.

Treatment planning algorithms can account for the capabilities of the specific radiation treatment system they are used with, for example, the energy spectrum and intensity profile of the radiation beam, and the capabilities of the MLC. Generally speaking, treatment planning algorithms proceed by calculating the radiation dose received by each voxel in the treatment volume, adjusting one or more variable system parameters, such as the angle of irradiation or the positions of the MLC leaves, and then recalculating the dose received by each voxel. This process is ideally performed iteratively until an optimized plan is reached. However, the amount of time needed to perform the large number of calculations for each iteration places a practical limit on the number of iterations that can be performed. Accordingly, the algorithm is terminated after a predetermined amount of time, after a predetermined number of iterations, or after some other practical limit is reached. Generally speaking, there is a tradeoff between the accuracy and speed of the different algorithms available for treatment planning.

III. Conflicts in Concurrent Treatment of Multiple Treatment Targets

Figure 6:
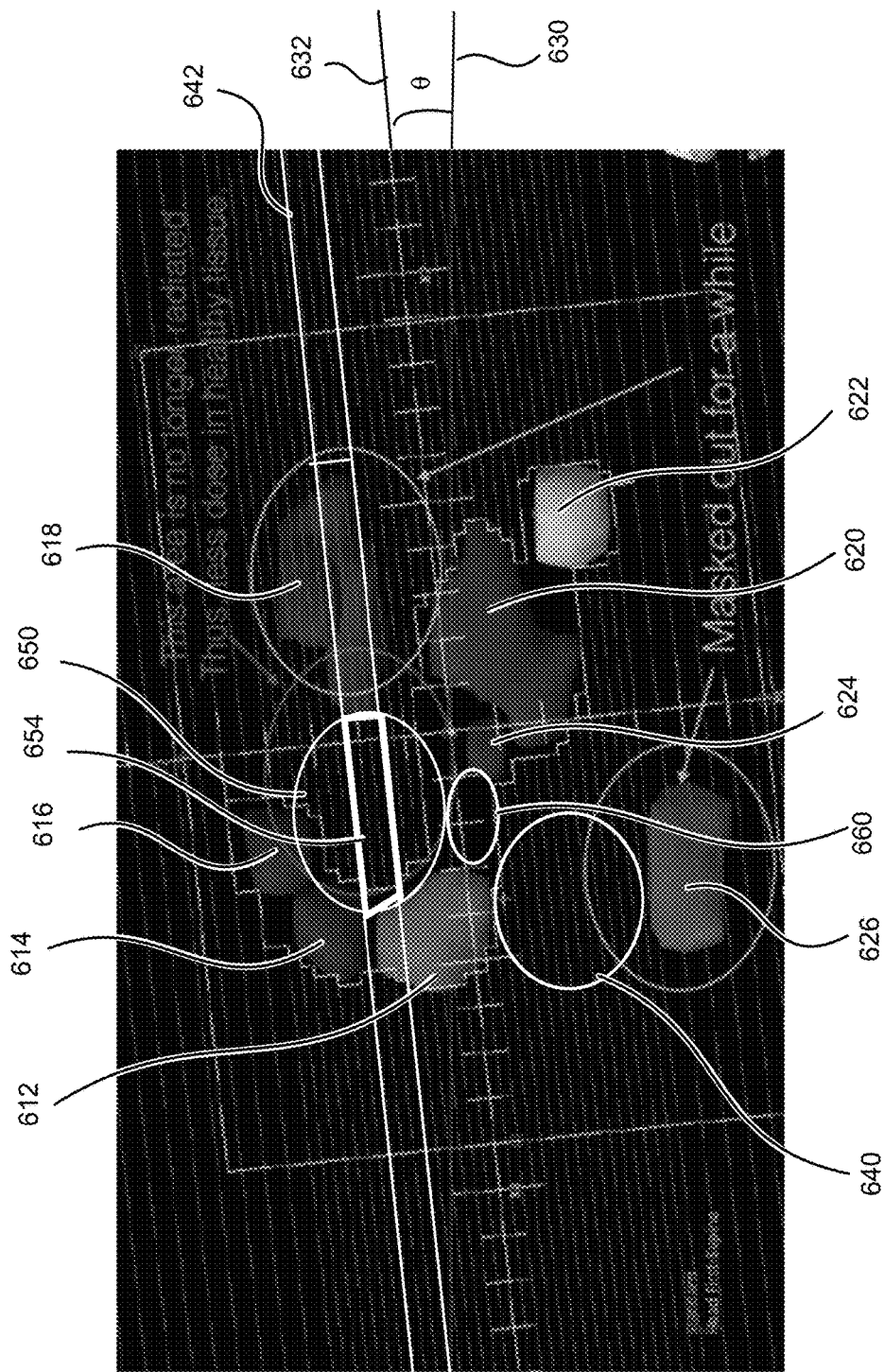
FIG. 6 shows an exemplary beam's-eye view (BEV) of a treatment area of a patient.

In cases where a tumor has metastasized, there may be multiple treatment targets within a treatment area of a patient. FIG. 6 shows an exemplary beam's-eye view (BEV) of a treatment area (e.g., a cranial region) of a patient. As illustrated, there are a number of metastasis targets in the treatment area, such as the three medium-size targets 612, 614, and 616 on the upper left hand side, a doublet 618 on the upper right hand side, a large target 620 below the doublet 618, a small target 624 to the left of the target 620, a medium size target 622 to the lower right of the target 620, and another target 626 at the lower left.

When treating multiple targets concurrently using volumetric modulated arc therapy (VMAT), a conflict may arise when there are more than one targets under a single pair of leaves in the multi-leaf collimator (MLC). For instance, consider the example illustrated in FIG. 6. Here, the direction of MLC leaf motion is along the axis 632, corresponding to a collimator angle of θ (e.g., 5 degrees) with respect to the horizontal axis 630. As can be seen, both the target 612 and the doublet 618 lie under the leaf pair 642, and there is an interstitial region 654 between these two targets in the direction of leaf motion. Thus, if the opening for the leaf pair 642 is wide enough such that both the target 612 and the doublet 618 are exposed to radiation at the same time, the normal tissue in the interstitial region 654 will also be exposed to radiation. Therefore, a choice may need to be made in determining the leaf sequences as which one of the two targets 612 and 618 to expose to radiation at a given time.

It should be noted that a conflict between two targets may arise only when an interstitial region between the two targets is in the direction of leaf motion. For instance, in the example illustrated in FIG. 6, the interstitial region 650 is in the direction of leaf motion, and therefore may give rise to a conflict. On the other hand, the interstitial region 640 between the target 612 and the target 626 is not in the direction of leaf motion, and thus may not give rise to a conflict.

IV. Collimator Angle Optimizer

Typically, planners of VMAT-based stereotactic radiosurgery (SRS) treatments set collimator angles for each arc by visual inspection or by convention. However, in the presence of multiple targets, two or more targets may fall under a given pair of MLC leaves whereby an optimizer for a radiation treatment plan may be left with the choice of which target to expose to radiation or whether to expose more than one target to radiation. This effectively frustrates the optimizer and leads to an increase in normal-tissue exposure to radiation, and a decrease in conformity of dose about targets.

Figure 7:
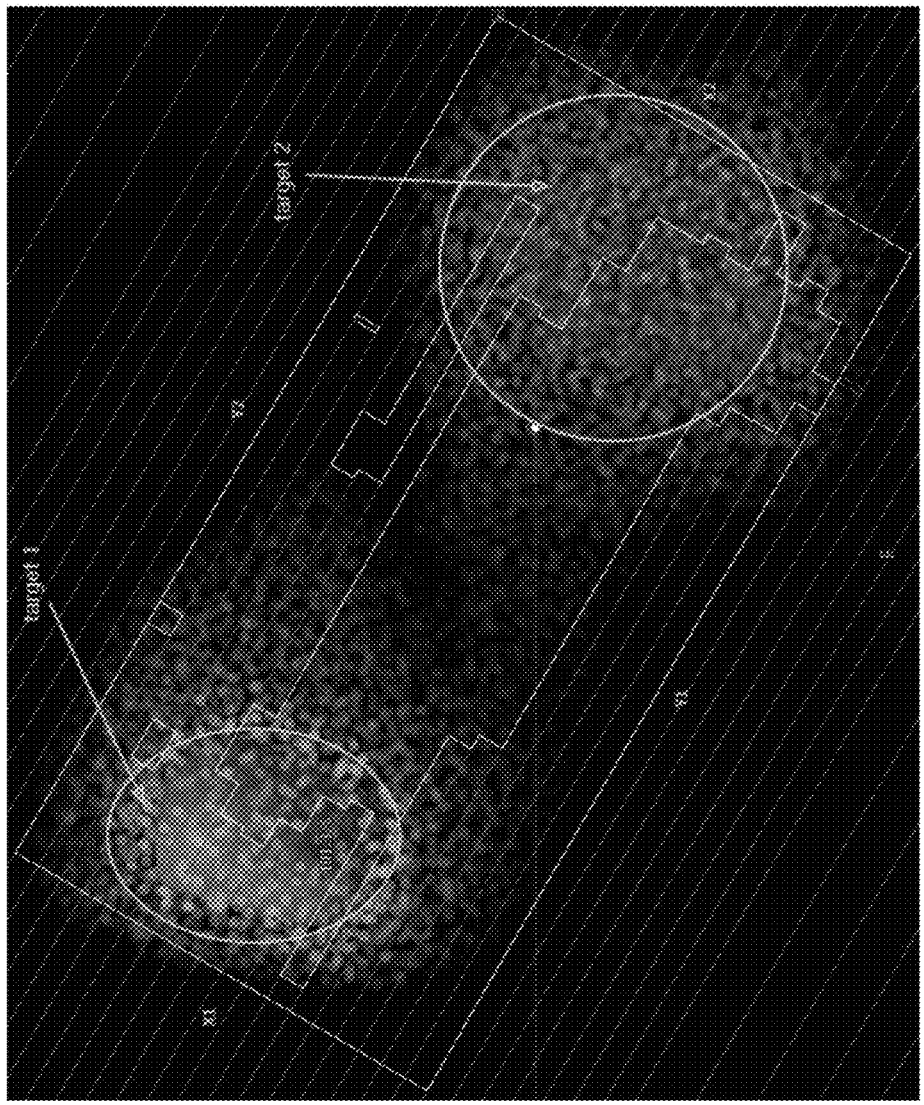
FIG. 7 shows an exemplary BEV of a treatment area of a patient with respect to a collimator angle.

FIG. 7 illustrates a situation where a non-optimal collimator angle has been chosen. The MLC leaves move in the direction of the blue lines. The open aperture between the targets leads to undesired exposure of normal tissue and hinders the generation of a conformal dose distribution about each target.

Embodiments can provide a means of treating multiple targets simultaneously during a VMAT arc as effectively, and as independently from one another, as possible. For example, for a given VMAT arc, embodiments can measure the total area accrued in the direction of motion of the MLC leaves that is formed between pairs of targets over the duration of the arc. This total area can also be referred to as the directional area or the interstitial area in the direction of leaf motion). The measurement can be performed for a range of trial collimator angles. In FIG. 7, which is in the beam's eye view, the directional area spans over several pairs of leaves and extends from target 1 to target 2. Ideally, the collimator angle for which the directional area is zero is one that allows each target to be irradiated independently of others.

Figure 8:
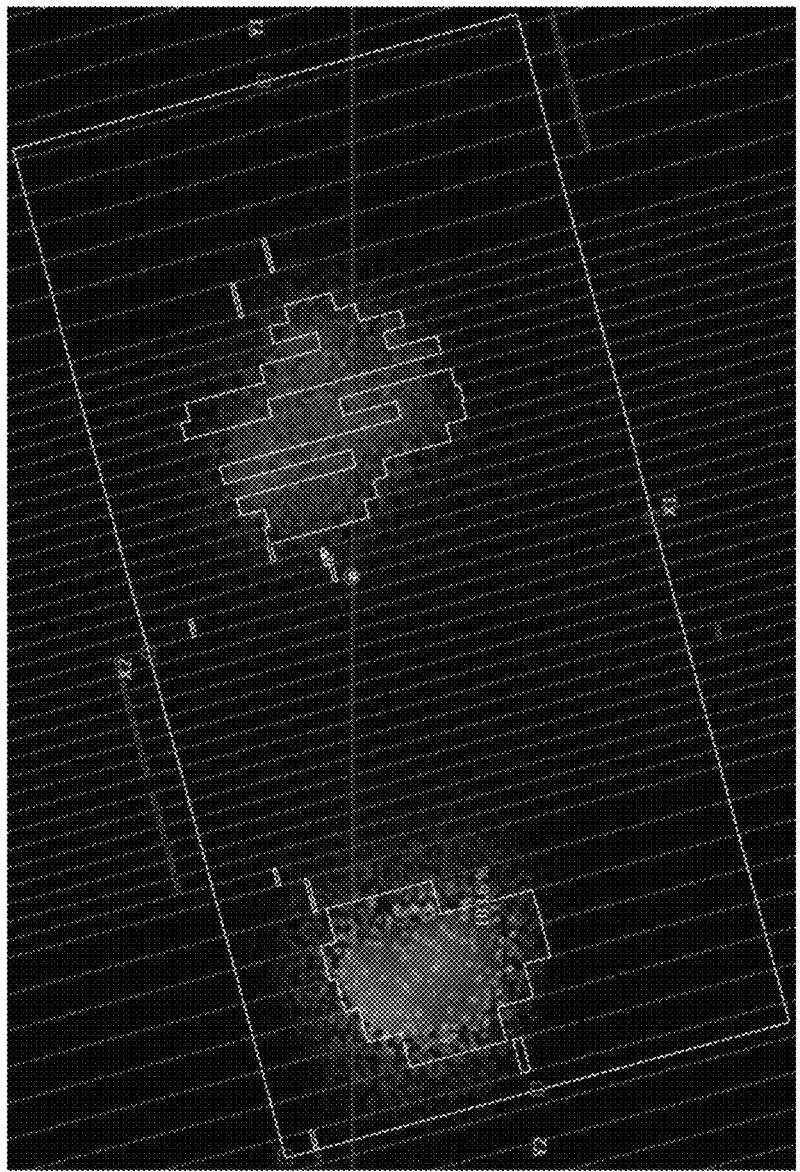
FIG. 8 shows an exemplary BEV of a treatment area of a patient with respect to another collimator angle according to an embodiment of the present invention.

FIG. 8 illustrates an example of a well-chosen collimator angle, where the "directional area" is zero. The MLC leaves delineate the shape of the targets and undesired exposure of normal tissue is minimized.

Embodiments can either take the actual MLC parameters (positions and widths of individual leaves) into account or it can be employed in a generic, geometric fashion that has a virtual MLC leaf width of, e.g., 1.25 mm. Embodiments may also serve as a precursor for dynamic collimator angle optimization, where the collimator angle of a VMAT arc is allowed to vary during beam-on time.

Augmenting a VMAT optimizer with collimator angle optimization can spare organs at risk (OARs) close to targets better than, e.g., conformal arcs that do not modulate the MLC apertures. According to some embodiments, the collimator angle optimizer can be advantageous when applied to treating multiple (cranial) targets simultaneously with VMAT as it may improve normal tissue sparing between targets, and enable more conformal simultaneous treatment of multiple targets.

According to some embodiments, the measurement of the "directional area" accrued between clusters of targets over control points is generalized by utilizing mathematical transformations on the projected lengths of MLC leaves between targets. This facilitates calibration of the collimator angle optimizer such that it distinguishes optimal angles more clearly from suboptimal ones.

Embodiments may be applied to dynamic collimator angle optimization. The measurement of the directional area at different collimator angles over smaller arc sectors enables finding sector-specific, locally optimal collimator angles.

V. Couch Angle Optimizer

Figure 9:
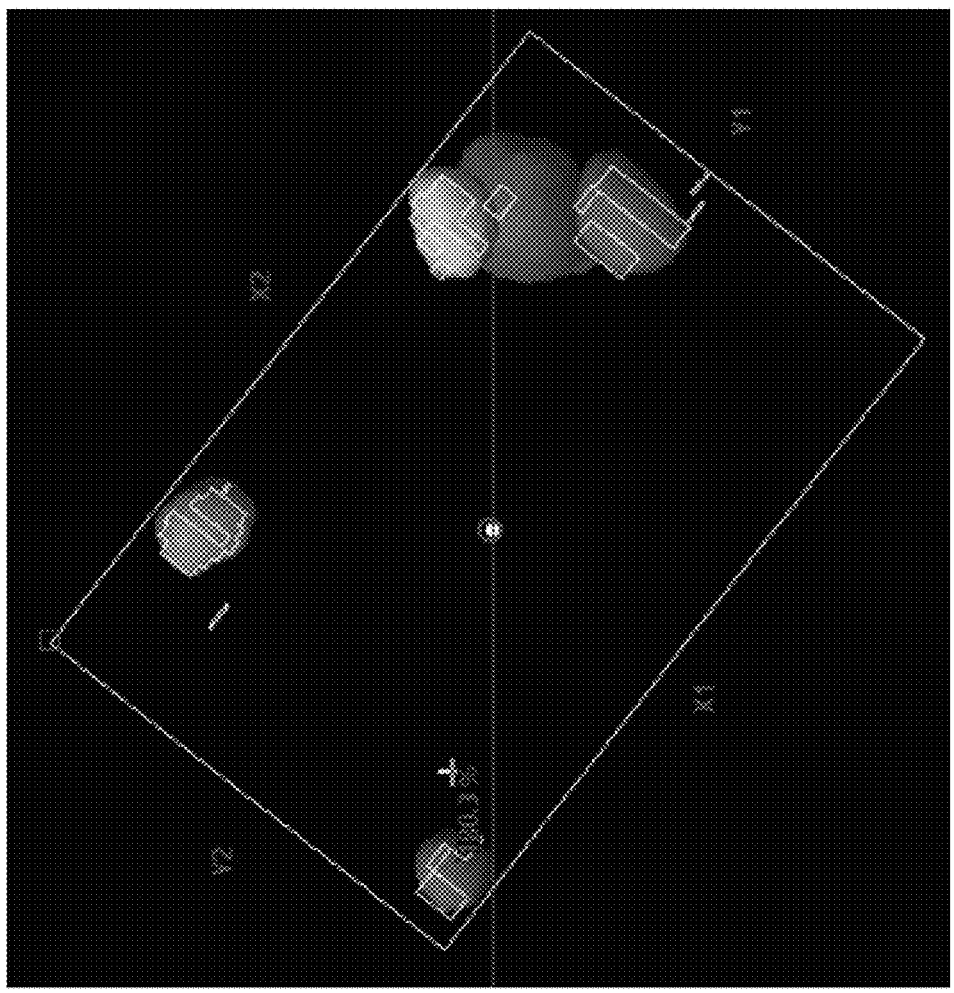
FIG. 9 shows an exemplary BEV of a treatment area of a patient with respect to a couch angle.

In treating multiple cranial targets concurrently with VMAT using single-isocenter stereotactic radiosurgery (SRS) or stereotactic body radiation therapy (SBRT), the targets typically stack on top of one another in the beam's eye view. FIG. 9 illustrates a situation where three targets fall on top of one another in the beam's eye view. This is largely because the angles to which the patient support (henceforth "the couch") is rotated, are often chosen by a protocol that is not patient-specific. The VMAT optimizer will then have to decide to what extent to irradiate all the stacking targets and the normal tissue and/or organs at risk located between the targets in the direction of the incident beam.

Figure 10:
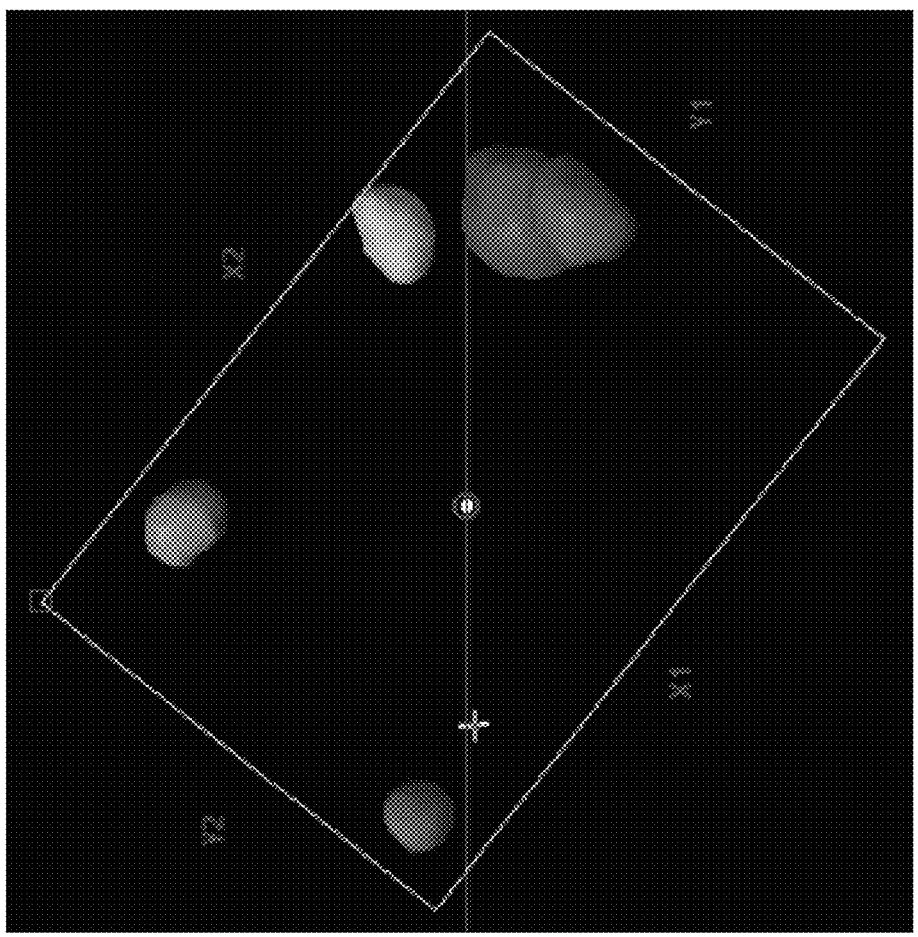
FIG. 10 shows an exemplary BEV of a treatment area of a patient with respect to another couch angle according to an embodiment of the present invention.

Embodiments can select optimal couch angles algorithmically such that targets stack up as little as possible. FIG. 10 illustrates an arrangement where a couch angle adjustment of 20 degrees from the case illustrated in FIG. 9 removes the three-target overlap altogether. The preconditions can be that the isocenter and the desired number of arcs (N) are given. One practical aspect is that embodiment can pick N couch rotation angles that are also sufficiently far apart from one another in order to maximize the number of directions of incidence.

Embodiments can reduce healthy-tissue exposure to radiation in treating multiple targets concurrently. Also, they can speed up the clinical workflow by automating plan geometry generation for single-isocenter SRS/SBRT cases.

In conventional methods, treatment planners have either resorted to a given protocol, or looked at the playback of tumor motion in beam's eye view and tried to pick the best couch rotation angles by naked eye.

According to some embodiments, a set of trial couch rotation angles is examined. For each trial angle, the amount of overlap between different targets in the beam's-eye-view projection is measured to determine a score that characterizes the optimality of the trial angle. The trial angles are then sorted based on the associated score and the best angles are picked such that there is a sufficient amount of separation between adjacent arcs.

Embodiments of the present invention may reduce healthy-tissue exposure to radiation by removing a factor leading to dose bridging between multiple targets, whose magnitude is not easily discernible by naked eye a priori to treatment planning. It may speed up clinical workflow by providing a step of automation in the plan geometry generation.

For instance, the characteristic score can incorporate: (a) the measure of the overlap between targets; (b) distance considerations that minimize irradiation through the brain by preferring rotation angles for which skin-to-target (or skin-to-isocenter) distance is small; and (c) OAR considerations, for example OAR in front of target, OAR between targets, or OAR behind target.

In some embodiments, the main factor in the score is (a). This is because multiple metastasis are typically scattered throughout the brain thus making the distances in (b) statistically equal, and the VMAT optimizer deals with (c) via MLC modulation. Moreover, by requiring a minimal couch angle difference of, e.g., 25 degrees, embodiments of the present invention may avoid picking the set {53, 58, 63} degrees of couch angles, as they represent essentially the same sector around the patient's head.

The specification of the treatment geometry for cranial SRS may be greatly simplified from the user's perspective. Having delineated the targets, chosen the isocenter and the number of arcs, the user can let the couch angle optimizer find the couch rotations and the collimator angle optimizer the collimator angles.

According to some other embodiments, one could move the couch and the gantry simultaneously in order to increase the search space for finding trajectories for which there is little target-target overlap.

VI. Dynamic Target Masker

As discussed above, conflicts in concurrent treatment of multiple targets may be mitigated to some extent by appropriately selecting a collimator angle and/or a couch angle. But in some cases, it may not be possible to prevent conflicts among all targets along a treatment path using a static collimator angle, or it may not be feasible to change collimator angle dynamically to prevent conflicts due to speed constraints of the treatment device.

For instance, in the example illustrated in FIG. 6, if the collimator is rotated 90 degrees from the position depicted in FIG. 6, the interstitial region 654 between the target 612 and 618 may no longer give rise to a conflict because it is no longer in the direction of leaf motion. However, at this new collimator angle, the interstitial region 640 between the target 612 and the target 626 is now in the direction of leaf motion and therefore may give rise to a conflict. Therefore, in some cases, it may not be possible to prevent conflicts among all targets along a treatment path using a static collimator angle. The same argument may apply to a dynamically rotating collimator angle. For example, at a given spatial point before the last spatial point in the sequence of spatial points, the conflict-mitigating collimator angle may be zero degree, and at the next spatial point, the conflict-mitigating collimator angle may be 90 degrees. Such a 90-degree rotation of the MLC between consecutive spatial points is likely to be prohibitive due to speed constraints of the treatment device.

Conflicts may be especially common in the case of a large number of targets. For example, consider a case where there are N=30 brain metastases. The number of unique groups of m targets is binomial (N, m) and the group may contain any number of targets from m=1 to m=N. For N=30, the total number of combinations is therefore the sum of binomials (30, m) for m=1 to m=30, which is equal to 1,073,741,823. That is, in the case of 30 brain metastases, there can be in excess of one billion choices at each control point of the trajectory which targets could be included in the MLC opening. In practice, the number of choices at a given control point may be limited by stacking or overlapping of targets in the beam's-eye-view projection (see FIG. 6) and various constraints such as MLC leaf positioning and/or leaf speed constraints due to MLC positions at the previous and next control point of the sequence.

In some existing approaches to prevent irradiation of normal tissue in concurrent treatment of multiple targets, all targets may be assigned to specific arcs and not necessarily treated by all arcs at the same time. In cases where multiple targets line up along the direction of motion of a leaf pair, which would cause the pair to open wide and also expose the healthy tissue between the targets, each leaf pair may be only allowed to expose one target at any time. (See, e.g., AUTOMATIC BRAIN METASTASES PLANNING, Clinical White Paper, BRAINLAB, www.brainlab.com/wp-content/uploads/2015/09/RT_WP_EN_Automatic-Brain-Metastases-Planning_Sep15_final1.pdf.) In such approaches, some targets may be completely neglected in a given arc, but are included in another arc traced in the opposite direction. For example, assuming that the total number of targets is N, m of the N targets, where 0<m<N, may be included in an arc traced in a "forward" direction; a complement set of targets that includes those of the N targets not among the m targets may be included in an arc traced in the "backward" direction. Thus, such methods may require twice as many arcs.

Embodiments can provide dynamic target masking (referred herein as DTM) to resolve conflicts in a non-global VMAT optimizer in a way that introduces aspects of global optimization. For instance, in the example illustrated in FIG. 6, the doublet 618 may be "masked out" over a range of consecutive spatial points along a treatment path so that only the targets 612, 614, 616, 620, 622, and 624 are exposed to radiation, and the doublet 618 is not exposed to radiation, as illustrated in FIG. 6. For a different range of spatial points along the treatment path, the targets 612, 614, and 616 may be masked out so that only the doublet 618 and the targets 620, 622, and 624 are exposed to radiation.

It may be helpful to distinguish between global and local optimization schemes for generating radiation treatment plans. Global optimization schemes may attempt to find a global optimum for a given set of optimization parameters. In a global optimization, the entire sequence of fluence maps and the MLC patterns may change from one iteration to another. A global optimization is aware of the state of the system everywhere in making changes to the entire sequence. On the other hand, local optimization schemes may progress by iteratively modifying a subset of the entire sequence of fluence maps and the MLC pattern, while keeping the sequence not in the subset constant.

The progressive-resolution optimizer (PRO) (see Karl Otto, "Volumetric modulated arc therapy: IMRT in a single arc, Med Phys. 2008 January; 35(1):310-7) and similar approaches are based on examining the problem at increasingly finer scale and making increasingly more local changes to the MLC sequence as the optimization progresses. As the local changes to the MLC sequence may not necessarily eliminate the globally most significant conflicts, local optimization schemes may be ill-equipped to resolve the conflicts in multi-target cases. The DTM methods according to embodiments of the present invention may resolve the problem by introducing a global irradiation metric that is monitored in conjunction with making local mutations to the MLC sequence. The global irradiation metric may guide the local changes to the MLC sequence to correspond to the globally most significant conflicts.

U.S. patent application Ser. No. 15/621,962 discusses an algorithm that may reduce the amount of conflict (referred to as "MLC contention") prior to MLC sequence and dose rate optimization either by finding a fixed collimator angle that reduces conflicts, or by finding a treatment device-compatible sequence of collimator angles the reduces conflicts. The algorithm disclosed therein also includes a feature that tries to maximize the magnitude of the solid angle from which a set of voxels of the treatment target are irradiated prior to MLC sequence and dose rate optimization.

Embodiments may perform target masking dynamically within a VMAT optimizer. A VMAT optimizer, be it global or non-global, is an advantageous phase in the treatment plan optimization for deciding where in the control point sequence and which targets to mask out and which to irradiate, as the optimizer has the most information (e.g., fluence, dose, dose rates, optimization objectives, and MLC and other mechanical constraints of the treatment device) for making the decision.

Embodiments may be able to resolve conflicts dynamically during the VMAT optimization, and can make use of the fluence, which may be based on user-specified optimization objectives. In some embodiments, a self-improving feedback loop may be included as follows.

(a) A decision to mask out some targets at some control points is made.
(b) The fluence and the MLC sequence in the mask-modified section is reoptimized, which may provide a subsequence candidate.
(c) The total cost function of the optimizer may be evaluated. If there is an improvement, the change may be kept and the actual MLC sequence may be modified according to the subsequence candidate.
(d) If at a later stage of the optimization, the metrics based on fluence, dose and the optimization objectives indicate that further improvement of the treatment plan is possible by canceling a previous masking, and it is possible in terms of the machine constraints, it can be done.

According to various embodiments, the dynamic masking may take into account the dose prescription and the volume of each participating target. Dynamic masking of various targets may be balanced to ensure that each target receives the prescribed dose and is irradiated from as many directions as possible so as to ensure dose conformity about each target.

In one embodiment, a more persistent interstitial region, i.e., an interstitial region that exists for a larger range of consecutive spatial points, may be ranked higher. In another embodiment, an interstitial region with a larger integrated area may be ranked higher. In some other embodiments, a multi-criteria sorting method may be used. According to some embodiments, participating targets associated with higher ranked interstitial regions may be masked with higher priority.

In one embodiment, for each interstitial region, masking choices are made such that the participating targets with the lowest remaining absolute dose difference (i.e., the difference between the prescribed dose and the current dose) are masked out the most. In an alternative embodiment, the differential dose may be characterized by using a surrogate, such as absolute fluence map differences of prescribed and current maps at some control points. The surrogate may include a mathematical transformation at the level of differences between pixel-specific values of the fluence maps, and a weighting map.

For instance, in the example illustrated in FIG. 6, assume that the constituent voxels of the doublet target 618 are irradiated multiple times from a multitude of directions. The characterization of the directions of incidence for each voxel of each target is referred to as the irradiation metric. Assume further that for the direction of incidence corresponding to FIG. 6, the doublet target 618's irradiation metric has a larger reserve of hit counts than those of the targets 612, 614, and 616. The masking choices may be made such that the doublet 618 is masked for a larger range of contiguous spatial points, while the targets 612, 614, and 616 are masked for a shorter range of contiguous spatial points where the conflict exists. The irradiation metric may strive to balance the masking such that no target's irradiation metric falls below a threshold. This can ensure that each of the participating targets receives its respective prescribed dose, and the dose distribution retains a high level of conformity about each target as the balancing ensures sufficient coverage of the angular space about each target voxel. In some embodiments, when the irradiation metric of a certain target would fall below the threshold from further masking at certain control points, the masking attempt is not permitted.

In a VMAT radiation treatment, the level of dose conformity about a target may depend on from how large a solid angle each constituent of a target structure is irradiated. The upper limit for the magnitude of the angular coverage is $4\pi$ steradians. In general, the higher the angular coverage, the better the dose conformity can be. According to one embodiment of the present invention, if the targets participating in a conflict have about an equal demand, which is quantified as a function of fluence and dose differential between actual dose and prescribed dose, for additional exposure to irradiation, the dynamic masking is applied to the target, whose directional reserve better allows the masking.

According to one embodiment of the present invention, dynamic masking may be balanced over a single contiguous range of spatial points where a conflict exists. For instance, in the example illustrated in FIG. 6, assume that the doublet 618 and the cluster of targets 612, 614, and 616 are in conflict for a contiguous range of spatial points from a starting spatial point to an end spatial point. In one embodiment, the doublet 618 may be masked for a first portion of the contiguous range of spatial points from the starting spatial point to an intermediate spatial point, while the targets 612, 614, and 616 are exposed to radiation. Then for a second portion of the contiguous range of spatial points from the intermediate spatial point to the end spatial point, the targets 612, 614, and 616 may be masked, while the doublet 618 is exposed to radiation.

According to another embodiment of the present invention, dynamic masking may be balanced over a plurality of contiguous ranges of spatial points. For instance, in the example illustrated in FIG. 6, assume that the doublet 618 and the cluster of targets 612, 614, and 616 are in conflict for a first contiguous range of spatial points and a second contiguous range of spatial points. This may occur, for example, when a treatment path spans 360 degrees. A conflict may exit in a first contiguous range of spatial points corresponding to a first range of incidence angles, and then reappear in a second contiguous range of spatial points corresponding to a second range of incidence angles opposite to the first range of incidence angles. According to an embodiment of the present invention, the doublet 618 may be masked for the first contiguous range of spatial points while the cluster of targets 612, 614, and 616 are exposed to radiation; and the cluster of targets 612, 614, and 616 may be masked for the second contiguous range of spatial points while the doublet 618 is exposed to radiation. In another embodiment, the doublet 618 may be masked for a first portion of the first contiguous range of spatial points, and the cluster of targets 612, 614, and 616 may be masked for a second portion of the contiguous range of spatial points as well as the second contiguous range of spatial points. Other variations are also possible. Any masking strategy must be permitted by the irradiation metric. That is, there must be sufficient reserve for masking out given targets at given control points in the corresponding target masks.

In some embodiments of the present invention, dynamic masking may be balanced at a global level over all conflicts among all targets. For instance, in the example illustrated in FIG. 6, the target 612 may not be masked in a conflict with the doublet 618 over one contiguous range of spatial points, and may be masked when it is in conflict with the target 624 over another contiguous range of spatial points.

In some embodiments, the transitions between participating targets are done synchronously with a dose calculation scheme, as may be done by the Progressive Multiresolution Optimization mode of Varian's Photon Optimizer.

According to another embodiment of the present invention, a method for determining MLC leaf sequences in a treatment plan may use avoidance structures. For example, target masker can be interpreted as having targets as avoidance structures that change over the duration of the arcs in the treatment plan.

A. Global Initialization

In some embodiments, a time-ordered sequence C of control points is denoted as $C=\{c_0, c_1, \ldots, c_N\}$. Each control point may define the direction from which the radiation is administered with respect the isocenter, the collimator angle, the dose rate, the number of monitor units (MUs) delivered between two consecutive control points, the positions of collimator jaws (if there are any), the positions of all leaves of the multi-leaf collimator (MLC), and the like. An MLC may delineate the apertures through which the treatment targets are irradiated in an external-beam radiation therapy. A valid control point sequence may be one that does not break any treatment device and/or other constraints.

Given a valid initial control point sequence $C_1$, $C_1$ may be such that, at each control point, all targets are within the MLC-delineated apertures to the extent that machine constraints allow. For example, machine constraints may provide an upper limit to the separation between the tips of a leaf pair of the MLC (e.g., 15 cm), which may be smaller than the span of the target projection onto the BEV plane in the direction of leaf motion (e.g., 15.5 cm).

According to some embodiments, for $C_1$, a bookkeeping record that maintains an irradiation metric for each target of how select voxels of each target structure can be irradiated directionally may be established. With its maximally target-exposing apertures, $C_1$ may provide an upper limit for the metric albeit in the presence of conflicts between treatment targets. The upper bound may be referred to as the directional reserve.

In one embodiment, the select voxels can be all target voxels. In another embodiment, the select voxels may be a subset of PTV voxels that are uniformly distributed within the PTV. In some embodiments, the irradiation metric may include the number of control points from which a face of a cubic PTV voxel is hit, where the hit count is kept for each face of the voxel. Cube mapping methods may be employed to keep a more detailed record of from which sector on the surface of a unit sphere centered at the center of the voxel the voxel may be irradiated. The irradiation metric may, in addition to the directional component, contain other information such as distance from the surface of the patient's body to the voxel along the vector from the radiation source to the PVT voxel.

B. Identifying Conflicts Among Multiple Targets

As the control point sequence $C_1$ is given, all locations of possible conflicts may be ascertained, which may be indexed using the letter i, prior to optimization of the leaf sequences and of the amount of monitor units (MUs) between consecutive control points. A record may be kept of the time of appearance $t_{a,i}$ of time-areas $A_i$, and the time of disappearance $t_{d,i}$, the pair of target clusters $\{ID1_i, ID2_i\}$ between which the time-area $A_i$ is, and of the time-dependent set $L_i(t)$ of MLC leaf indices that can partake of the formation of the time-area $A_i$. The area subtended by the pair of target clusters $\{ID1_i, ID2_i\}$ in the direction of MLC leaf motion may be referred herein as an intertitial region.

FIGS. 11A-11D illustrate schematically an exemplary time dependence of $L_i(t)$, from the appearance to the disappearance of a conflict in a time series in the BEV perspective. Moving through the control point sequence in radiation order, the BEV projection changes from FIG. 11A to FIG. 11D. In this example, a first target cluster $ID1_i$ may include the target 1110, and a second target cluster $ID2_i$ may include the targets 1120 and 1130. The MLC leaf motion is along the X-axis.

Figure 11A:
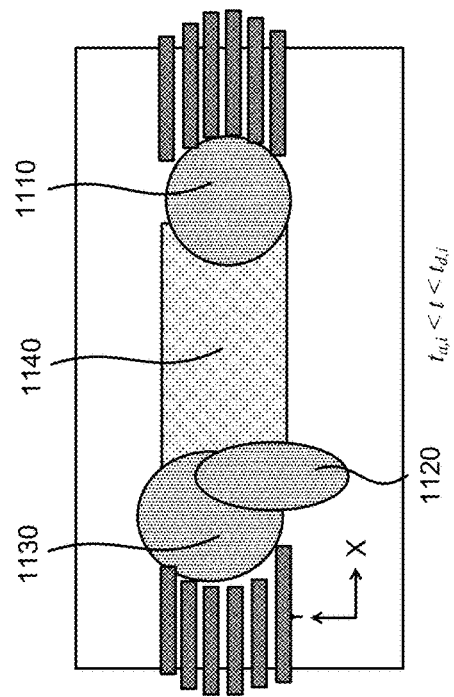
FIGS. 11A-11D illustrate schematically the appearance and disappearance of a possible conflict between two clusters of targets in a time series in the BEV perspective.

At the time of appearance $t=t_{a,i}$ at a first control point as illustrated in FIG. 11A, only a first leaf pair 115a and 1150b partakes in the conflict between the first target cluster $ID1_i$ and the second target cluster $ID2_i$; i.e., if the first leaf pair 1150a and 1150b is open wide enough to expose both the first target cluster $ID1_i$ and the second target cluster $ID2_i$ to radiation, the normal tissue in the intertitial region 1140 subtended between the first target cluster $ID1_i$ and the second target cluster $ID2_i$, i.e., the time-area $A_i(t=t_{a,i})$, may also be exposed to radiation. Thus, the time-dependent set $L_i(t=t_{a,i})$ may include only the first leaf pair 1150a and 1150b.

Figure 11B:
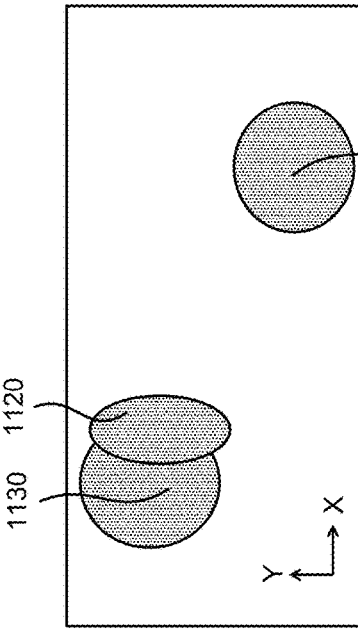

At an intermediate time $t_{a,i} < t < t_{d,i}$ at a second control point as illustrated in FIG. 11B, more leaf pairs may partake in the conflict, as the interstitial region 1140 subtended between the first target cluster $ID1_i$ and the second target cluster $ID2_i$, i.e., the time-area $A_i(t_{a,i} < t < t_{d,i})$, becomes wider in the direction normal to the direction of leaf motion (i.e., along the Y-axis). Thus, the time-dependent set $L_i(t_{a,i} < t < t_{d,i})$ may include, for example, six leaf pairs, as illustrated in FIG. 11B.

Figure 11C:
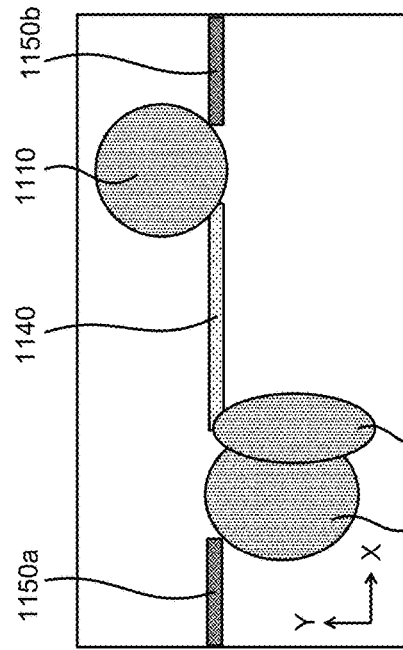
Figure 11D:
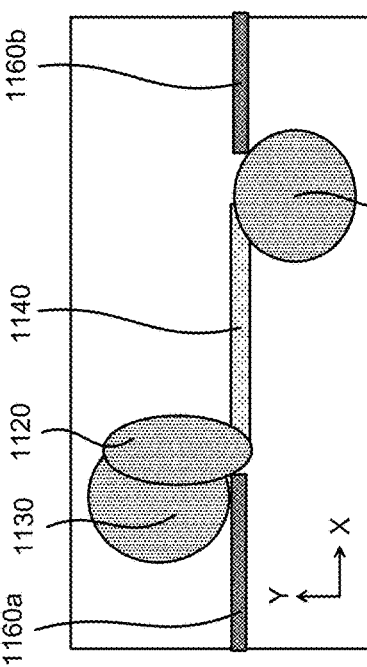

At the time of disappearance $t=t_{d,i}$ at a third control point as illustrated in FIG. 11C, only a second leaf pair 1160a and 1160b partakes in the conflict. Thus, the time-dependent set $L_i(t=t_{d,i})$ may include only the second leaf pair 1160a and 1160b. At a time $t > t_{d,i}$, at a fourth control point as illustrated in FIG. 11D, the conflict may disappear; i.e., there is no leaf pair partaking in a conflict.

Figure 12A:
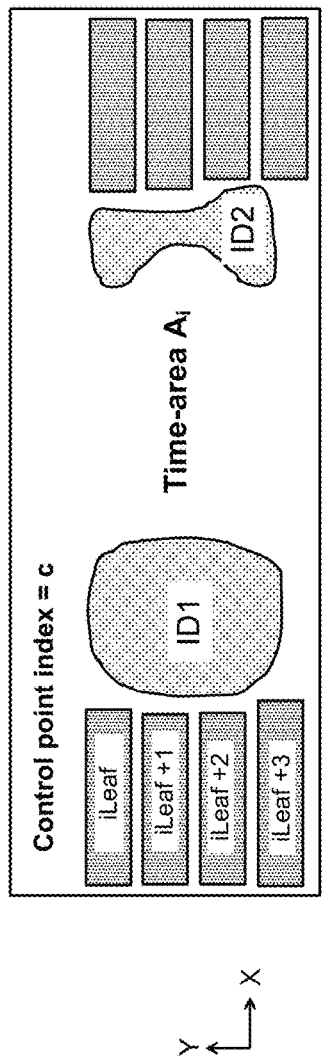
FIGS. 12A and 12B illustrate schematically how different control points in a treatment trajectory may provide different views of the projected targets.
Figure 12B:
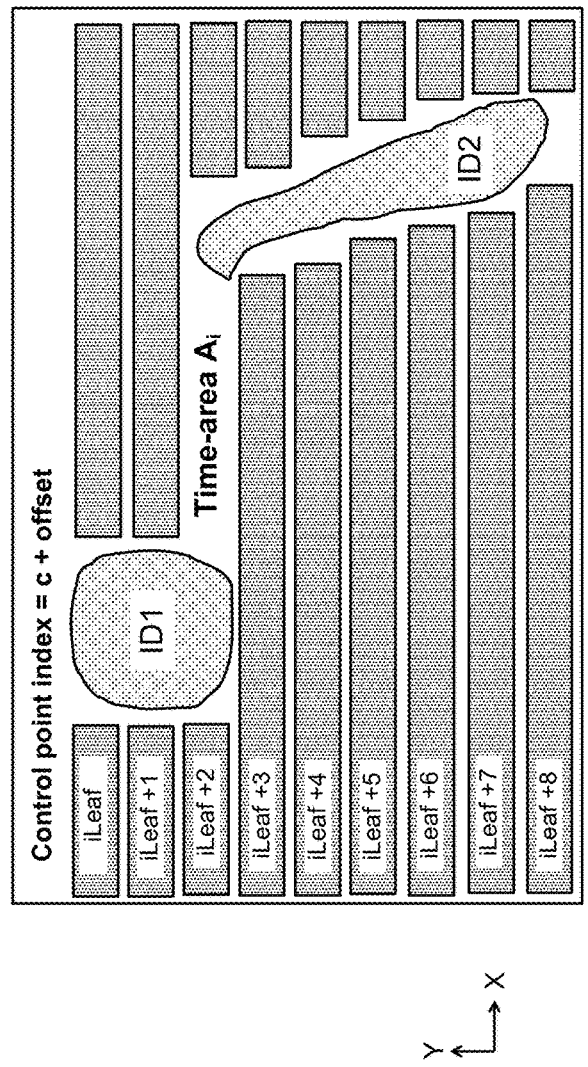

In some cases, each control point in the treatment trajectory may provide a different view of the projected targets. FIGS. 12A and 12B illustrate schematically another exemplary time dependence of $L_i(t)$ of a conflict in the BEV perspective at a first control point index c and a second control point index c+offset, respectively. The BEVs show a first target ID1 and a second target ID2. As illustrated, the projection of the second target ID2 at the first control point index c may be quite different from the projection at the second control point index c+offset. As the target projections change in the BEV over time t, the set of leaves $L_i(t)$ associated with the time-area $A_i(t)$ may change over time t as well. As illustrated in FIG. 12A, the set of leaf pairs that delineate time-area $A_i$ at the first control point index c between the first target ID1 and the second target ID2 may include $\{iLeaf+k\}$, where k=0, 1, 2, and 3. As illustrated in FIG. 12B, the set of leaves that delineate time-area $A_i$ at the second control point index c+offset between the first target ID1 and the second target ID2 may include $\{iLeaf+2\}$.

According to some embodiments, one may also keep track of the magnitude of the area during the lifetime of the conflict (i.e., from $t_{a,i}$ to $t_{d,i}$), such that the magnitude of the time-area can be evaluated as, $$A_i = \int_{t_{a,i}}^{t_{d,i}} A_i(t) dt. \tag{1}$$

In one embodiment, the integral in Eq. (1) may be approximated with a sum over control points. More generally, one may evaluate $A_i(t)$ as the magnitude of a transformation over the MLC leaves participating in the area formation:

$$A_i(t) = \sum_{l=l_{m(t)}}^{l_{M(t)}} f(s_l) w_l, \tag{1}$$

where $l_{m(t)}$ and $l_{M(t)}$ are the respective minimum and maximum leaf pair indices participating in the area formation at time t, and $w_l$ denotes the leaf width in leaf pair l in a direction perpendicular to the direction of leaf motion (e.g., along the Y-axis). The function f denotes a transformation, which in some embodiments may read f(x)=x. The symbol $s_l$ denotes the length of the segment along leaf pair l between the participating target clusters.

Note that the set $\{A_i\}$ of time-areas provides only a reference of time areas for the sequence $C_l$ that has maximally target-exposing apertures. The presence of conflicts is determined periodically at some iterations during the optimization from the actual control point sequence. The set $\{A_i\}$ may be employed as a reference to guide the search for the most significant conflicts.

C. Dynamic Masking Strategies

Figure 13:
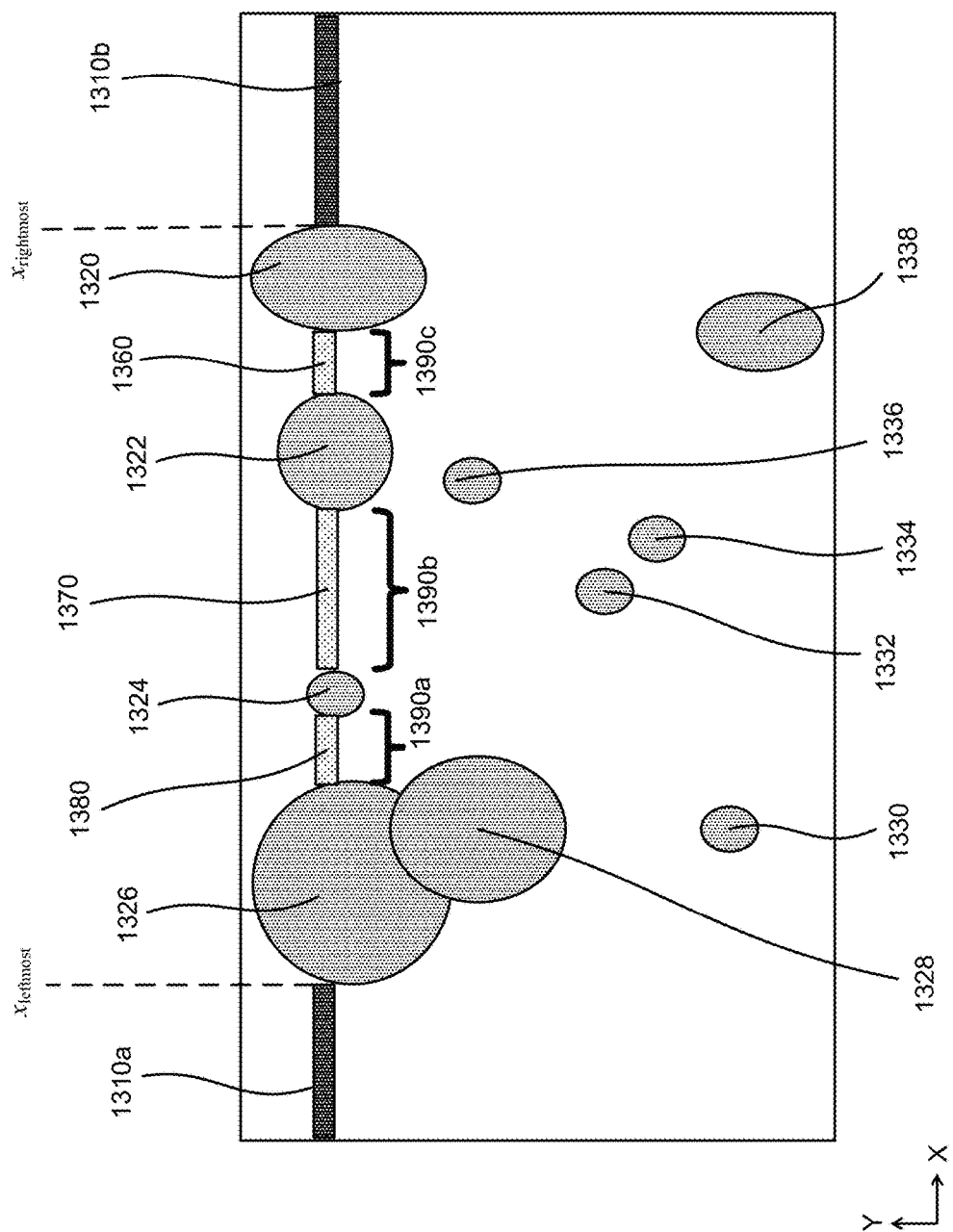
FIGS. 13-15 illustrate schematically a masking strategy in a concurrent treatment of multiple targets according an embodiment of the present invention.

A masking strategy may include dynamically removing and reintroducing various targets from and to the BEV projections at some control points. FIG. 13 shows schematically an exemplary BEV projection of multiple targets 1320, 1322, 1324, 1326, 1328, 1330, 1332, 1334, 1336, and 1338, illustrating a masking strategy according an embodiment of the present invention. As illustrated, a first target 1320, a second target 1322, a third target 1324, and a fourth target 1326 may participate in one or more conflicts under the leaf pair 1310a and 1310b. For example, if the leaf pair 1310a and 1310b are open wide enough such that both the first target 1320 and the fourth target 1326 can be exposed to radiation, the normal tissues in the interstitial regions 1360, 1370, and 1380 subtended between the first target 1320 and the second target 1322, between the second target 1322 and the third target 1324, and between the third target 1324 and the fourth target 1326, respectively, may also be exposed to radiation.

A masking strategy may instruct which of those targets participating in a conflict are removed from the target masks in order to resolve the conflict in a MLC leaf sequence. Referring to FIG. 13, on the row of the mask corresponding to a given MLC leaf pair l (e.g., the leaf pair 1310a and 1310b), the leftmost coordinate $x_{leftmost}$ denoting target location is the leftmost coordinate the leaf pair l is allowed to expose to radiation, and the rightmost coordinate $x_{rightmost}$ denoting target location is the rightmost coordinate the leaf pair l is allowed to expose to radiation. Note that, withing the interval $[x_{leftmost}, x_{rightmost}]$, there may be multiple sub-intervals at $[x_{lift}^{(k)}, x_{right}^{(k)}]$, k=0, 1, 2, . . . , (e.g., sub-intervals 1390a-1390c,) that correspond to target positions in the BEV projection.

Figure 14:
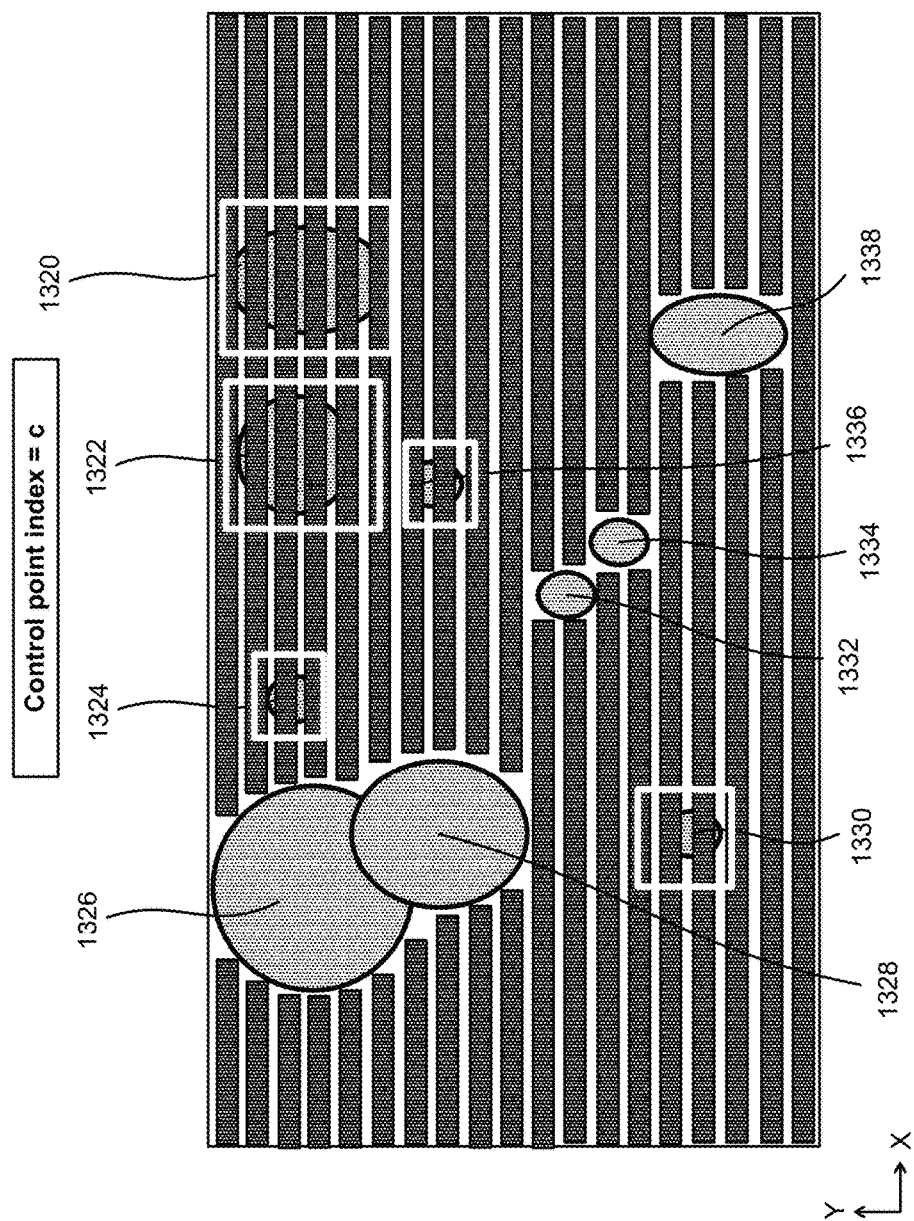
Figure 15:
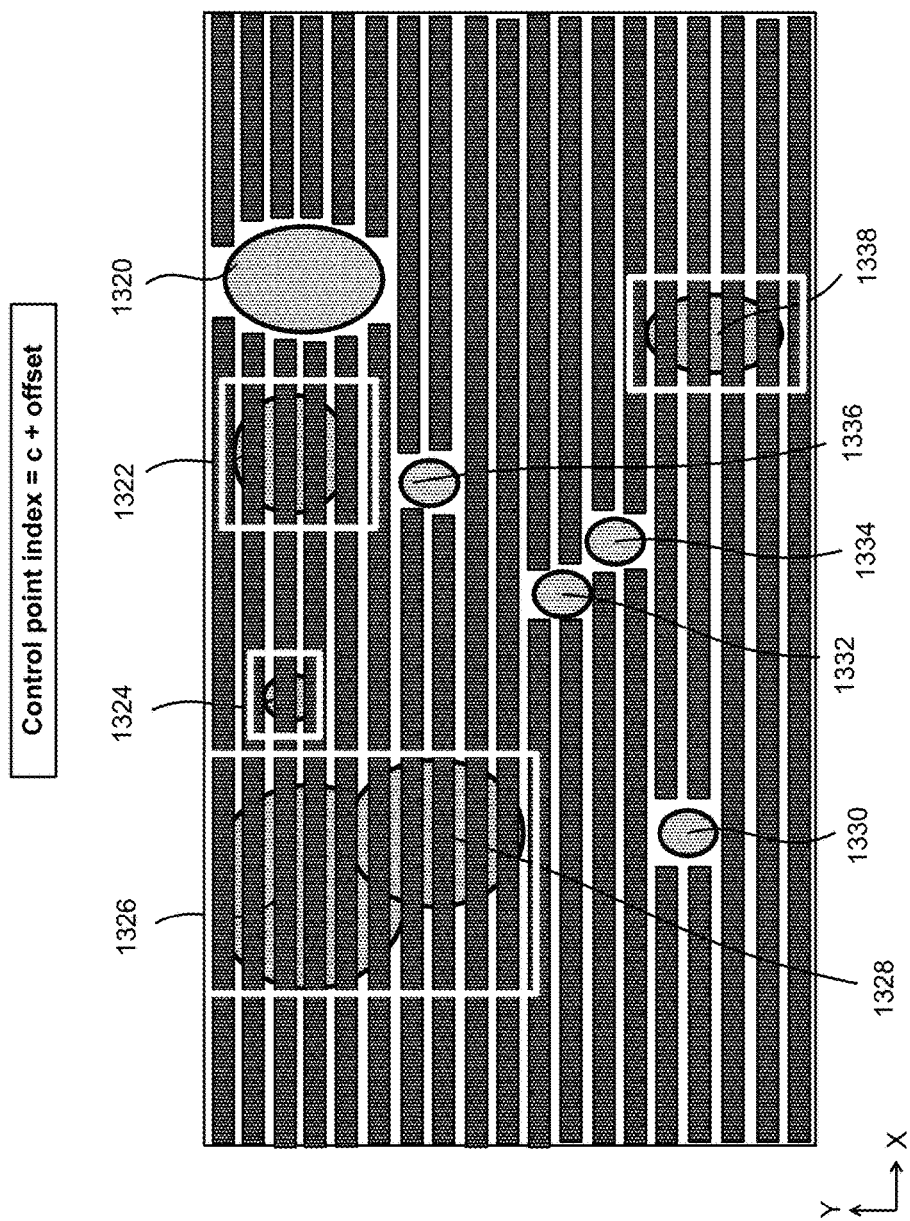

According to some embodiments, the removal and possible reintroduction of targets may be carried out dynamically during an optimization. For example, as illustrated in FIG. 14, for a certain range of control points, the MLC leaf sequences may be configured such that targets 1320, 1322, 1324, 1330, and 1336 are removed from the BEVs (i.e., "masked"), so that only the targets 1326, 1328, 1332, 1334, and 1338 can be exposed to radiation. In this manner, radiation to normal tissues in the instertial areas subtended between conflicting targets may be prevented. For another range of control points in the lifetimes of the conflicts, some of the masked targets may be reintroduced into the BEVs, and some of the targets that are previously unmasked may be masked. For example, as illustrated in FIG. 15, the previously unmasked targets 1326, 1328, and 1338 are now masked, and the previously masked targets 1320 and 1330 are reintroduced.

In some embodiments, at iteration s of the optimization, one may populate a set $\{A_i^{(s)}\}$ of time-areas, where i is the conflict index, for the actual control point sequence similarly to the method described above. The population of the listing may be guided by the locations of potential conflicts in the set $\{A_i\}$ based on $C_1$.

The masking strategy may subject to a visibility constraint. In some embodiments, it may be assumed that there is a maximal amount of masking that can be done relative to the directional reserve based on $C_1$. For example, the visibility constraint may stipulate that any non-zero hit count to any face of a select PTV voxel can be reduced at most by X %, where X could be e.g. 25, and must be kept at least at unity. In some other embodiments, the visibility constraint may stipulate that any non-zero hit count to any solid-angle sector about the select voxel in a cube-mapping strategy can be reduced at most by X %.

In one embodiment, an end condition for stopping of any further masking may be a depleted directional reserve. A depleted directional reserve is one in which any additional masking would lead to violation of the visibility constraint. All masking strategies that do not violate the visibility constraint can be considered as valid.

D. Methods of Dynamic Masking of Targets

Figure 16:
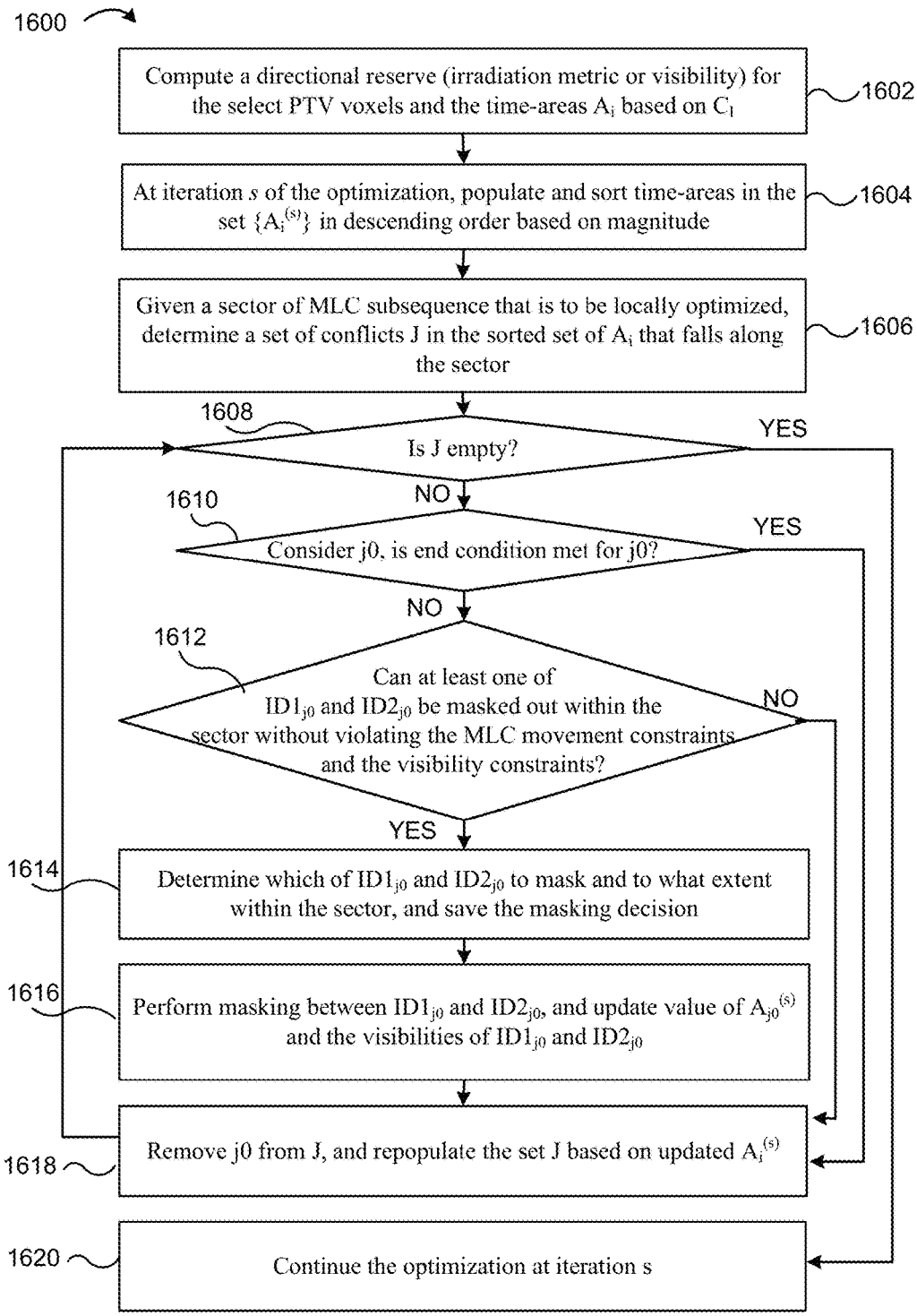
FIG. 16 shows a flowchart illustrating a method of marking strategy according to some embodiments of the present invention.

FIG. 16 shows a flowchart illustrating a method 1600 of marking strategy according to some embodiments of the present invention.

At 1602, before iterations of a VMAT optimization, the directional reserve (referred to as "irradiation metric" or "visibility") for the select PTV voxels and the time-areas $A_i$ are computed based on $C_1$. This step may be referred to as global initialization as discussed above.

At 1604, at iteration s of the optimization, time-areas $A_i^{(s)}$ are populated and sorted based on magnitude in descending order into sequence $\tilde{A}_i^{(s)}$. "Populating" refers to the process of mining through BEV projections for the MLC sequence at iteration s and finding any conflicts. The conflicts in the set $\{A_i^{(s)}\}$, as well as other associated variables, are recorded. Set i=1, which corresponds to the largest time-area (possibly transformed by f of Eq. (1)).

At 1606, given a sector of a contiguous MLC subsequence (e.g., a sector of a VMAT arc) that is to be locally optimized, one may examine which conflicts in $\{\tilde{A}^{(s)}\}$ fall along the sector to determine a set of conflicts J. The conflicting leaf pairs may be indexed using $j \in J$.

Figure 17:
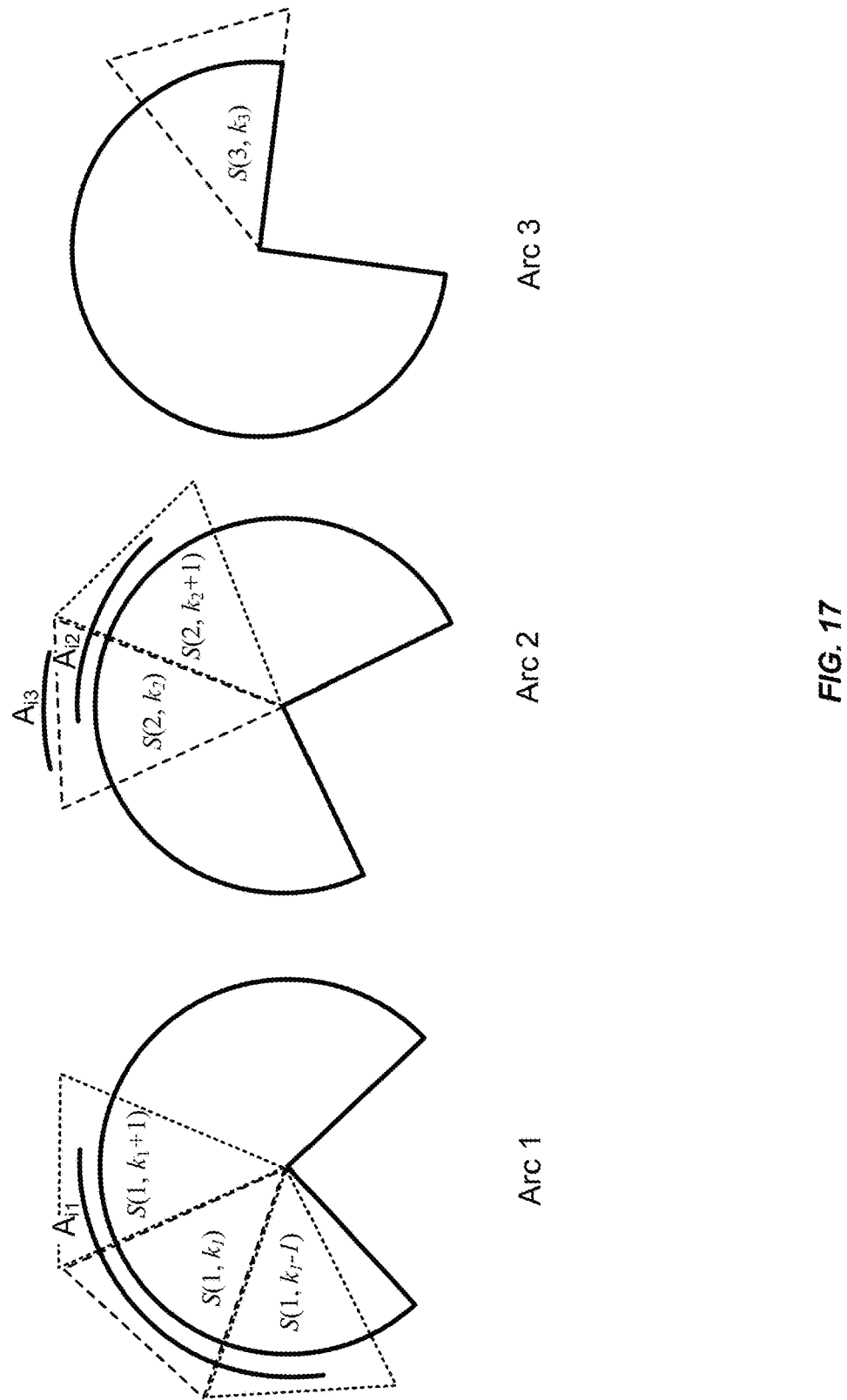
FIG. 17 illustrates the relationship between sectors of VMAT arcs and conflicts according to some embodiments.

FIG. 17 illustrates the relationship between sectors of VMAT arcs and conflicts according to some embodiments. The notation S(a, k) refers to sector a of an arc (i.e., trajectory) with index k. Each sector S(a, k) may correspond to a subsequence of control points. In the examples illustrated in FIG. 17, conflict $A_{i_1}$ spans sectors $S(1, k_1-1)$, $S(1, k_1)$, and $S(1, k_1+1)$.

Conflict $A_{i_2}$ spans sectors $S(2, k_2)$ and $S(2, k_2+1)$. Conflict $A_{i_3}$ fits inside sector $S(2, k_2)$. There is no conflict in sector $S(3, k_3)$. In some embodiments, each sector may be locally optimized.

Referring again to FIG. 16, at 1608, one may determine whether the set J is empty (1608).

At 1620, if it is determined that the set J is empty (i.e., there is no conflict), the optimization at iteration s may be continued.

At 1610, if J is not empty, conflict j0 within the set J is considered, where j0 is the index corresponding to the largest time-area in the set J. It may be determined whether the end condition is met for j0. As discussed above, in some embodiments, an end condition for stopping of any further masking may be a depleted directional reserve (a depleted directional reserve may be one in which any additional masking would lead to violation of the visibility constraint).

At 1612, if the end condition is not met for j0, it may be determined whether at least one of the participating clusters $ID1_{j0}$ and $ID2_{j0}$ can be masked out within the sector without violating leaf movement constraints and the visibility constraints.

At 1614, if it is determined that at least one of the participating clusters $ID1_{j0}$ and $ID2_{j0}$ can be masked out within the sector without violating leaf movement constraints and the visibility constraints, it may be determined which of $ID1_{j0}$ and $ID2_{j0}$ to mask and to what extent within the sector. The masking decision is then saved. In some embodiments, masking decisions may be determined based on the fluence demands in the contiguous MLC subsequence to the targets in the clusters $ID1_{j0}$ and $ID2_{j0}$, so as to examine which of $ID1_{j0}$ and $ID2_{j0}$ could benefit more from additional irradiation. The other one can be masked away while respecting the visibility constraints.

At 1616, masking between $ID1_{j0}$ and $ID2_{j0}$ may be performed according to the masking decision for $ID1_{j0}$ and $ID2_{j0}$ within $[t_{a,i_0}, t_{d,i_0}]$ for one of the clusters at a time. The value of $\tilde{A}_{j_0}^{(s)}$ and the values of any other conflicts that are resolved may then be updated. If the resolution breaks a conflict into multiple unresolved subparts, the conflicts for the new subparts in the set $\{A_i^{(s)}\}$ is recorded, and the visibilities of $ID1_{j0}$ and $ID2_{j0}$ are updated. For instance, in the examples illustrated in FIG. 7, if $A_{i_1}$ is resolved only within $S(1, k_1)$, there may be two unresolved subparts of the conflict $A_{i_1}$: one in $S(1, k_1-1)$, and another in $S(1, k_1+1)$.

At 1618, j0 is removed from the set J, and the set J is repopulate based on updated $A_i^{(s)}$. The method 1600 may then loop back to step 1608 to consider a next j0 in the updated set J.

If it is determined at step 1610 that the end condition is met for j0 (e.g., a depleted directional reserve), or if it is determined at step 1612 that neither of $ID1_{j0}$ and $ID2_{j0}$ can be masked without violating leaf movement constraints and the visibility constraints, the method 1600 may proceed to step 1618 to remove j0 from the set J, and repopulate the set J based on updated $A_1^{(s)}$ (1618).

In some embodiments, if a conflict is found to span more than one contiguous sector of a VMAT arc, the remaining parts of the conflict residing in the non-active sector(s) (i.e., sectors that are not currently being optimized) may be tagged for high-priority resolution when those sectors are optimized.

Figure 18:
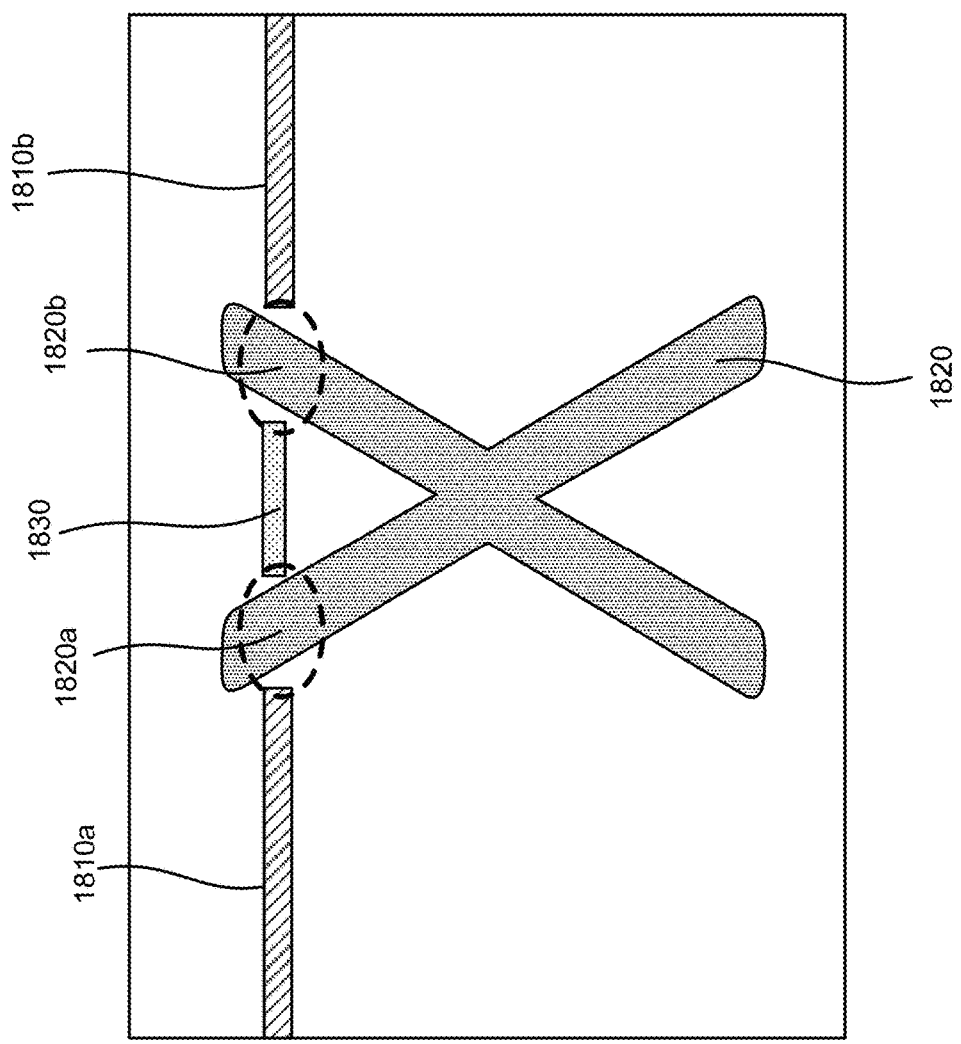
FIG. 18 illustrates schematically how a conflict may arise from two disjoint parts of a single target.

In some cases, a conflict may arise between two parts of a same target. For instance, in the example illustrated in FIG. 18, the BEV of the projection of the target 1820 at a certain control point may have two disjoint parts 1820a and 1820b under a single leaf pair 1810a and 1810b. The two disjoint parts 1820a and 1820b of the target 1820 may be in conflict if the leaf pair 1810a and 1810b is opened wide enough to expose both parts to irradiation, as the normal tissue in the interstitial region 1830 subtended by the two parts may also be irradiated. In such cases, the dynamic target masker may assign a unique ID to each spatially disjoint interval in the direction of leaf motion at each control point.

In some cases, a planner may designate N spatially disjoint targets as a single target structure. In such cases, the dynamic target masker may also assign a unique ID to each spatially disjoint target.

Figure 19:
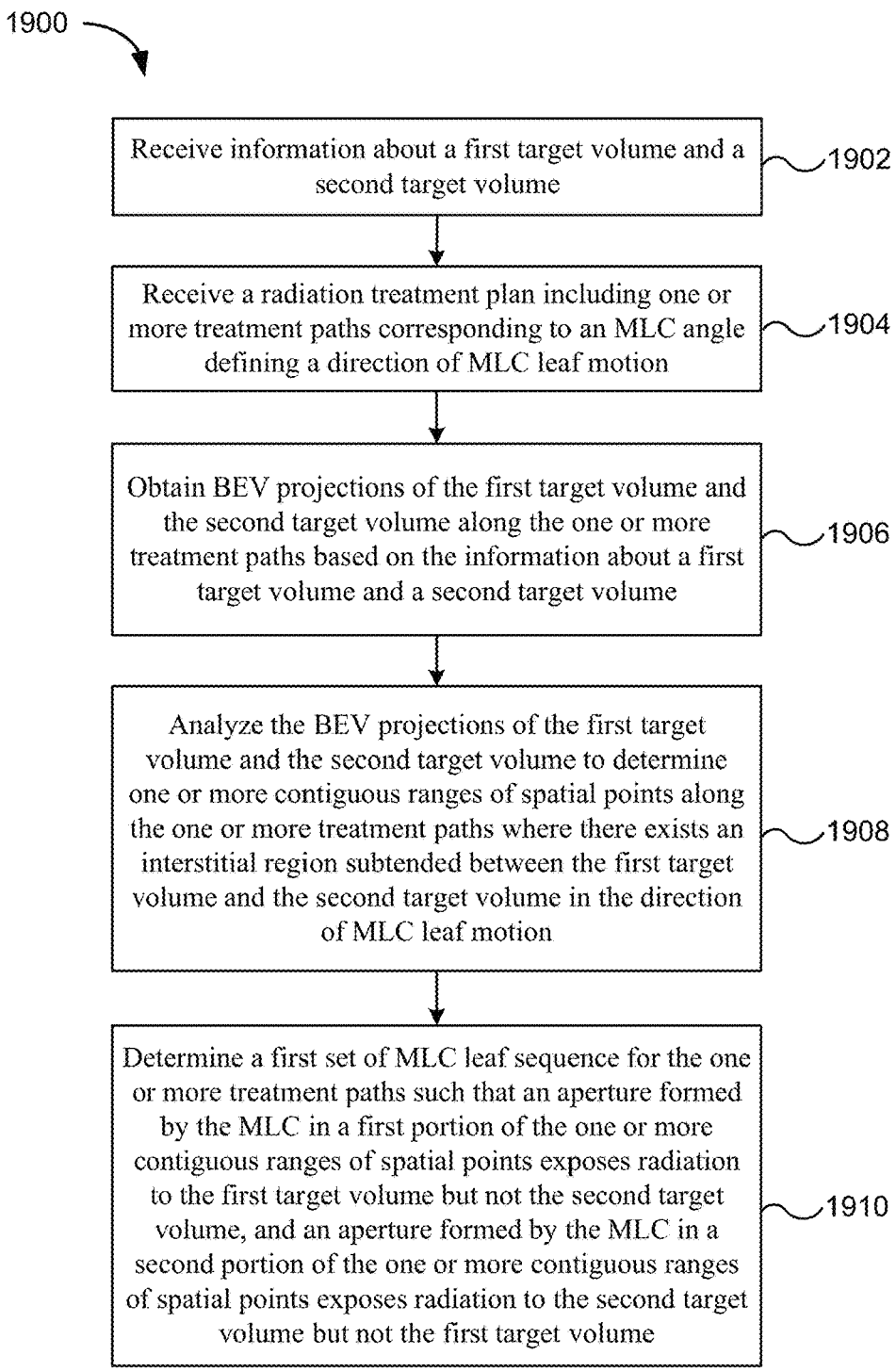
FIG. 19 shows a simplified flowchart illustrating a method for determining multi-leaf collimator (MLC) leaf sequences in a radiation treatment plan for concurrent treatment of multiple targets according to some embodiments of the present invention.

FIG. 19 shows a simplified flowchart illustrating a method 1900 for determining multi-leaf collimator (MLC) leaf sequences in a radiation treatment plan for treating a plurality of target volumes within a treatment area of a patient using an external-beam radiation treatment system, according to an embodiment of the present invention.

At 1902, information about a first target volume and a second target volume is received.

At 1904, a radiation treatment plan is received at the computer system. The radiation treatment plan may include one or more treatment paths. Each treatment path may define a respective trajectory of spatial points. Each spatial point is associated with a set of values for treatment axes of the external-beam radiation treatment system. The one or more treatment paths may correspond to an MLC angle defining a direction of MLC leaf motion.

At 1906, BEV projections of the first target volume and the second target volume along the one or more treatment paths are obtained based on the information about a first target volume and a second target volume.

At 1908, the BEV projections of the first target volume and the second target volume are analyzed to determine one or more contiguous ranges of spatial points along the one or more treatment paths where there exists an interstitial region subtended between the first target volume and the second target volume in the direction of MLC leaf motion.

At 1910, a first set of MLC leaf sequences for the one or more treatment paths is determined such that an aperture formed by the MLC in a first portion of the one or more contiguous ranges of spatial points exposes radiation to the first target volume but not the second target volume, and an aperture formed by the MLC in a second portion of the one or more contiguous ranges of spatial points exposes radiation to the second target volume but not the first target volume.

The radiation treatment plan as well as the first set of MLC leaf sequences may be transmitted to control circuitry of the external-beam radiation treatment system to cause the external-beam radiation treatment system to deliver radiation to the patient according to the one or more treatment paths and the MLC leaf sequence.

According to one embodiment, both the first portion and the second portion of the one or more contiguous ranges of spatial points are within a same contiguous range of spatial points. According to another embodiment, the first portion of the one or more contiguous ranges of spatial points is within a first contiguous range of spatial points, and the second portion of the one or more contiguous ranges of spatial points is within a second contiguous range of spatial points independent from the first contiguous range of spatial points.

In some embodiments, the first portion and the second portion of the one or more contiguous ranges of spatial points are determined such that each of the first target volume and the second target volume is irradiated from as many directions as possible over the one or more treatment paths.

Method 1900 may further include computing a first irradiation metric for the first target volume and a second irradiation metric for the second target volume. The first irradiation metric may relate to a number of spatial points along the one or more treatment paths from which the first target volume is exposed to radiation with maximal target-exposing MLC apertures. the second irradiation metric may relate to a number of spatial points along the one or more treatment paths from which the second target volume is exposed to radiation with maximal target-exposing MLC apertures. The first portion and the second portion of the one or more contiguous ranges of spatial points may be determined based at least in part on the first irradiation metric and the second irradiation metric. The method 1900 may further include updating the first irradiation metric and the second irradiation metric using the first set of MLC leaf sequence.

According to some embodiments, the first portion and the second portion of the one or more contiguous ranges of spatial points may be determined based on a volume of the first target volume and a volume of the second target volume. In one embodiment, the volume of the first target volume is greater than the volume of the second target volume, and the first portion and the second portion of the one or more contiguous ranges of spatial points are determined such that a length of the first portion is greater than a length of the second portion.

E. Synchronization of the Making Strategy with the Multi-Resolution Scheme in Progressive-Resolution Optimizer (PRO)

In some embodiments, dynamic masking transitions between participating target clusters may be carried out synchronously with the Progressive-Resolution Optimizer (PRO) described in U.S. Pat. No. 8,416,918, the content of which is incorporated herein by reference in its entirety. In the PRO, the machine configuration limits, such as maximum leaf speeds, are violated and corrected during the optimization of a treatment plan according to a predefined schedule. The predefined schedule may define at which stage of the optimization and by how much the machine limits may be violated. The violations may be corrected periodically in PRO such that the MLC leaf sequences may eventually meet all machine constraints. At the correction stages, there may exist a multitude of possible solutions to make the MLC leaf sequences fall within all machine limits. The dynamic masking strategy may be pursued and used at the correction stages of the PRO schedule, such that the resulting valid MLC leaf sequences are in accordance with the dynamic masking strategy. In other words, the corrections to the MLC leaf sequences are biased by the dynamic target masker. For instance, in the examples illustrated in FIG. 17, when the leaf sequences in $S(1, k_1)$ and $S(1, k_1 \pm 1)$ are corrected, the dynamic target masker may encourage a correction that results in the resolution of conflict $A_{i_1}$ if permitted by mechanical constraints.

VII. Computer System

Figure 20:
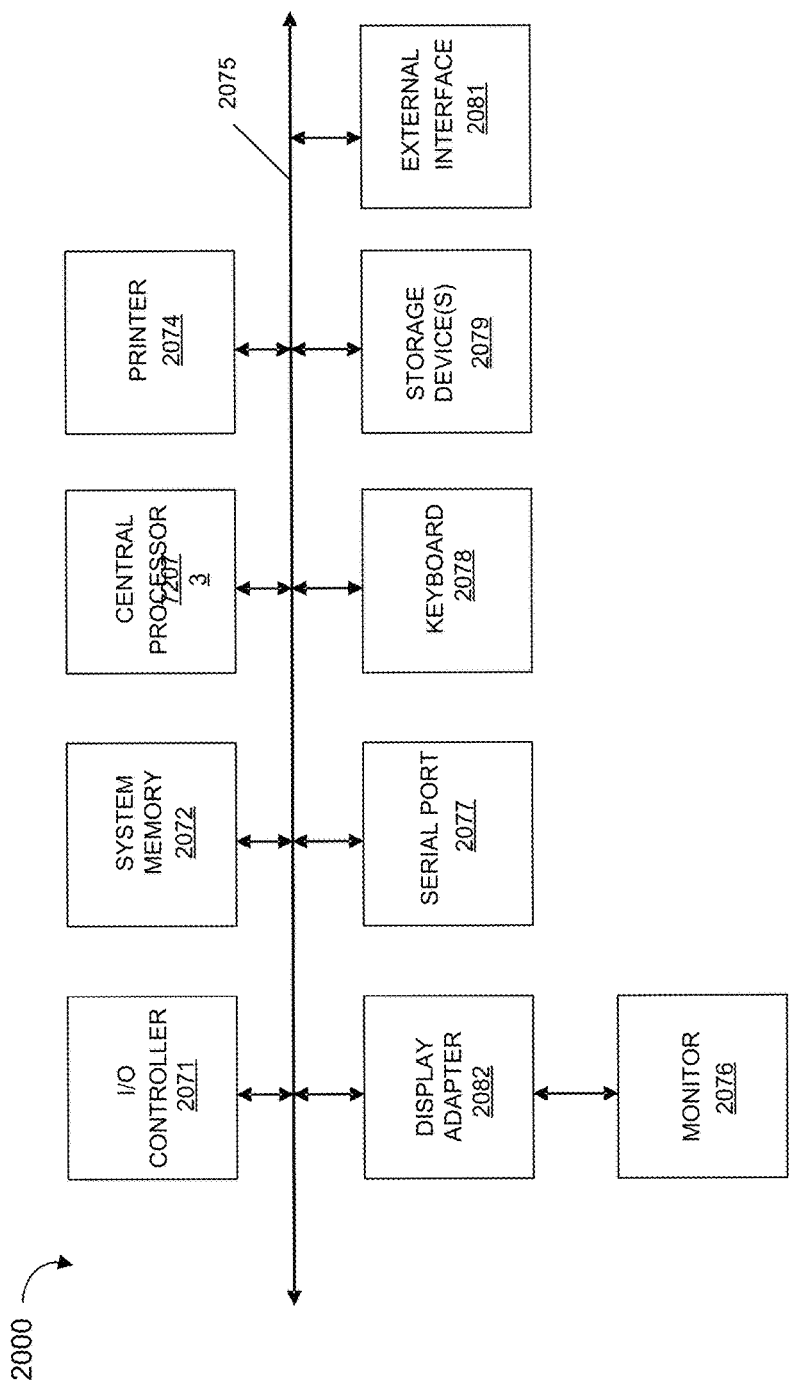
FIG. 20 shows a block diagram of an example computer system usable with system and methods according to embodiments of the present invention.

Any of the computer systems mentioned herein may utilize any suitable number of subsystems. Examples of such subsystems are shown in FIG. 20 in computer system 2000. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 20 are interconnected via a system bus 2075. Additional subsystems such as a printer 2074, keyboard 2078, storage device(s) 2079, monitor 2076, which is coupled to display adapter 2082, and others are shown. Peripherals and input/output (I/O) devices, which couple to I/O controller 2071, can be connected to the computer system by any number of means known in the art, such as serial port 2077. For example, serial port 2077 or external interface 2081 (e.g. Ethernet, Wi-Fi, etc.) can be used to connect computer system 2000 to a wide area network such as the Internet, a mouse input device, or a scanner. The interconnection via system bus 2075 allows the central processor 2073 to communicate with each subsystem and to control the execution of instructions from system memory 2072 or the storage device(s) 2079 (e.g., a fixed disk, such as a hard drive or optical disk), as well as the exchange of information between subsystems. The system memory 2072 and/or the storage device(s) 2079 may embody a computer readable medium. Any of the data mentioned herein can be output from one component to another component and can be output to the user.

A computer system can include a plurality of the same components or subsystems, e.g., connected together by external interface 1281 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

External interface 1281 can be used to transmit one or more treatment plans to one or more radiation treatment devices, as described herein. For example, a treatment planning application can reside on a server computer, and a client computer can use the treatment planning application. The server computer can be part of a cloud computing platform that provides software as a service (SaaS). Once a treatment plan is determined, a client computer can specify which radiation device or a treatment plan database accessible by the radiation device for transmitting one or more files encapsulating the treatment plan. For instance, an IP address can be specified.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned here are incorporated by reference in their entirety for all purposes. None is admitted to be prior art.

What is claimed is:

1. A method for determining multi-leaf collimator (MLC) leaf sequences in a radiation treatment plan for treating a plurality of target volumes within a treatment area of a patient using an external-beam radiation treatment system, the method comprising:
   receiving, by a computer system, information about a first target volume and a second target volume of the plurality of target volumes;
   receiving, by the computer system, the radiation treatment plan including one or more treatment paths, each treatment path defining a respective trajectory of spatial points, and each spatial point associated with a set of values for treatment axes of the external-beam radiation treatment system, wherein the one or more treatment paths correspond to an MLC angle defining a direction of MLC leaf motion;
   obtaining, by the computer system, beam's-eye view (BEV) projections of the first target volume and the second target volume along the one or more treatment paths based on the information about a first target volume and a second target volume;
   analyzing, by the computer system, the BEV projections of the first target volume and the second target volume to determine one or more contiguous ranges of spatial points along the one or more treatment paths where there exists an interstitial region subtended between the first target volume and the second target volume in the direction of MLC leaf motion; and
   determining, by the computer system, a first set of MLC leaf sequences for the one or more treatment paths such that an aperture formed by the MLC in a first portion of the one or more contiguous ranges of spatial points exposes radiation to the first target volume but not the second target volume, and an aperture formed by the MLC in a second portion of the one or more contiguous ranges of spatial points exposes radiation to the second target volume but not the first target volume.

2. The method of claim 1, further comprising transmitting the radiation treatment plan including the first set of MLC leaf sequences to control circuitry of the external-beam radiation treatment system to cause the external-beam radiation treatment system to deliver radiation to the patient according to the one or more treatment paths and the first set of MLC leaf sequences.

3. The method of claim 1, wherein both the first portion and the second portion of the one or more contiguous ranges of spatial points are within a same contiguous range of spatial points.

4. The method of claim 1, wherein:
   the first portion of the one or more contiguous ranges of spatial points is within a first contiguous range of spatial points; and
   the second portion of the one or more contiguous ranges of spatial points is within a second contiguous range of spatial points independent from the first contiguous range of spatial points.

5. The method of claim 1, wherein the first portion and the second portion of the one or more contiguous ranges of spatial points are determined such that each of the first target volume and the second target volume is irradiated from as many directions as possible over the one or more treatment paths.

6. The method of claim 1, further comprising:
   computing a first irradiation metric for the first target volume and a second irradiation metric for the second target volume, wherein the first irradiation metric relates to a number of spatial points along the one or more treatment paths from which the first target volume is exposed to radiation with maximal target-exposing MLC apertures, and wherein the second irradiation metric relates to a number of spatial points along the one or more treatment paths from which the second target volume is exposed to radiation with maximal target-exposing MLC apertures, and
   wherein the first portion and the second portion of the one or more contiguous ranges of spatial points are determined based at least in part on the first irradiation metric and the second irradiation metric.

7. The method of claim 6, further comprising updating the first irradiation metric and the second irradiation metric using the first set of MLC leaf sequences.

8. The method of claim 1, wherein the first target volume is within a first target, and the second target volume is within a second target spatially disjoint from the first target.

9. The method of claim 1, wherein the first target volume and the second target volume are within a first target.

10. The method of claim 9, wherein the first target comprises a spatially contiguous region, and wherein the first target volume and the second target volume are within the spatially contiguous region.

11. The method of claim 9, wherein the first target comprises a first region and a second region spatially disjoint from the first region, the first target volume is within the first region, and the second target volume is within the second region.

12. The method of claim 1, wherein the one or more treatment paths comprise one or more volumetric modulated arc therapy (VMAT) arcs.

13. An external-beam radiation treatment system comprising:
a radiation treatment device including:
a rotatable gantry including a treatment head and a multi-leaf collimator (MLC), wherein the MLC is configured to shape a radiation beam emitted from the treatment head; and
a control unit configured to:
control rotation of the rotatable gantry;
control emission of the radiation beam from the treatment head; and
control a shape of the radiation beam via the MLC;
one or more processors; and
a non-transitory computer readable medium storing a plurality of instructions that when executed control the one or more processors to determine MLC leaf sequences in a radiation treatment plan for treating a plurality of target volumes within a treatment area of a patient, the instructions comprising:
receiving, by a computer system, information about a first target volume and a second target volume of the plurality of target volumes;
receiving, by the computer system, the radiation treatment plan including one or more treatment paths, each treatment path defining a respective trajectory of spatial points, and each spatial point associated with a set of values for treatment axes of the external-beam radiation treatment system, wherein the one or more treatment paths correspond to an MLC angle defining a direction of MLC leaf motion;
obtaining, by the computer system, beam's-eye view (BEV) projections of the first target volume and the second target volume along the one or more treatment paths based on the information about a first target volume and a second target volume;
analyzing, by the computer system, the BEV projections of the first target volume and the second target volume to determine one or more contiguous ranges of spatial points along the one or more treatment paths where there exists an interstitial region subtended between the first target volume and the second target volume in the direction of MLC leaf motion;
determining, by the computer system, a first set of MLC leaf sequences for the one or more treatment paths such that an aperture formed by the MLC in a first portion of the one or more contiguous ranges of spatial points exposes radiation to the first target volume but not the second target volume, and an aperture formed by the MLC in a second portion of the one or more contiguous ranges of spatial points exposes radiation to the second target volume but not the first target volume; and
delivering, by the treatment head of the radiation treatment device, radiation to the patient according to the one or more treatment paths of the radiation treatment plan using the first set of MLC leaf sequences.

14. The external-beam radiation treatment system of claim 13, wherein both the first portion and the second portion of the one or more contiguous ranges of spatial points are within a same contiguous range of spatial points.

15. The external-beam radiation treatment system of claim 13, wherein:

the first portion of the one or more contiguous ranges of spatial points is within a first contiguous range of spatial points; and
the second portion of the one or more contiguous ranges of spatial points is within a second contiguous range of spatial points independent from the first contiguous range of spatial points.

16. The external-beam radiation treatment system of claim 13, wherein the first portion and the second portion of the one or more contiguous ranges of spatial points are determined such that each of the first target volume and the second target volume is irradiated from as many directions as possible over the one or more treatment paths.

17. The external-beam radiation treatment system of claim 13, wherein the instructions further comprises:
computing a first irradiation metric for the first target volume and a second irradiation metric for the second target volume, wherein the first irradiation metric relates to a number of spatial points along the one or more treatment paths from which the first target volume is exposed to radiation with maximal target-exposing MLC apertures, and wherein the second irradiation metric relates to a number of spatial points along the one or more treatment paths from which the second target volume is exposed to radiation with maximal target-exposing MLC apertures, and
wherein the first portion and the second portion of the one or more contiguous ranges of spatial points are determined based at least in part on the first irradiation metric and the second irradiation metric.

18. The external-beam radiation treatment system of claim 17, wherein the instructions further comprises updating the first irradiation metric and the second irradiation metric using the first set of MLC leaf sequences.

19. A computer product comprising a non-transitory computer readable medium storing a plurality of instructions that when executed control a computer system to determine MLC leaf sequences in a radiation treatment plan for treating a plurality of target volumes within a treatment area of a patient using an external-beam radiation treatment system, the instructions comprising:
receiving, by the computer system, information about a first target volume and a second target volume of the plurality of target volumes;
receiving, by the computer system, the radiation treatment plan including one or more treatment paths, each treatment path defining a respective trajectory of spatial points, and each spatial point associated with a set of values for treatment axes of the external-beam radiation treatment system, wherein the one or more treatment paths correspond to an MLC angle defining a direction of MLC leaf motion;
obtaining, by the computer system, beam's-eye view (BEV) projections of the first target volume and the second target volume along the one or more treatment paths based on the information about a first target volume and a second target volume;
analyzing, by the computer system, the BEV projections of the first target volume and the second target volume to determine one or more contiguous ranges of spatial points along the one or more treatment paths where there exists an interstitial region subtended between the first target volume and the second target volume in the direction of MLC leaf motion; and
determining, by the computer system, a first set of MLC leaf sequences for the one or more treatment paths such that an aperture formed by the MLC in a first portion of the one or more contiguous ranges of spatial points exposes radiation to the first target volume but not the second target volume, and an aperture formed by the MLC in a second portion of the one or more contiguous ranges of spatial points exposes radiation to the second target volume but not the first target volume.

20. The computer product of claim 19, wherein the instructions further comprises transmitting the radiation treatment plan including the first set of MLC leaf sequences to control circuitry of the external-beam radiation treatment system to cause the external-beam radiation treatment system to deliver radiation to the patient according to the one or more treatment paths and the first set of MLC leaf sequences.

* * * * *